(12) United States Patent
Cihak et al.

(10) Patent No.: US 11,864,784 B2
(45) Date of Patent: Jan. 9, 2024

(54) PIN DRIVE ROTARY SURGICAL CUTTING TOOLS AND POWERED HANDPIECES

(71) Applicant: Medtronic PS Medical, Inc., Fort Worth, TX (US)

(72) Inventors: Paul Cihak, Euless, TX (US); Zachary Heiliger, Golden, CO (US)

(73) Assignee: Medtronic PS Medical, Inc., Fort Worth, TX (US)

( * ) Notice: Subject to any disclaimer, the term of this patent is extended or adjusted under 35 U.S.C. 154(b) by 435 days.

(21) Appl. No.: 17/132,223

(22) Filed: Dec. 23, 2020

(65) Prior Publication Data

US 2021/0106350 A1 Apr. 15, 2021

Related U.S. Application Data

(63) Continuation of application No. 16/106,597, filed on Aug. 21, 2018, now Pat. No. 10,905,453, which is a
(Continued)

(51) Int. Cl.
*B23B 31/00* (2006.01)
*B23B 31/107* (2006.01)
(Continued)

(52) U.S. Cl.
CPC .... *A61B 17/32002* (2013.01); *A61B 17/1615* (2013.01); *B23B 31/005* (2013.01);
(Continued)

(58) Field of Classification Search
CPC ............... B23B 31/005; B23B 31/008; B23B 2231/0244; B23B 31/1071; B23B 2231/0264; B23B 2231/22
See application file for complete search history.

(56) References Cited

U.S. PATENT DOCUMENTS

| 233,709 A | 10/1880 | Starr |
| 288,676 A | 11/1883 | Stearns |
(Continued)

FOREIGN PATENT DOCUMENTS

| CH | 686113 A5 | 1/1996 |
| CN | 1150073 A | 5/1997 |
(Continued)

OTHER PUBLICATIONS

Korean Office Action 10-2017-7027832 dated Jan. 6, 2023.
(Continued)

*Primary Examiner* — Eric A. Gates
(74) *Attorney, Agent, or Firm* — Carter, DeLuca & Farrell LLP

(57) ABSTRACT

A surgical cutting tool includes an elongated shaft and a cutting head. The shaft defines a coupling portion terminating at a proximal end of the shaft, a stem portion, and a distal portion. The stem portion defines a central axis. The coupling portion optionally defines a deflection surface positioned oblique with respect to the central axis and connected with a first driven surface and a second driven surface. Upon insertion into a drive chuck, the deflection surface promotes self-alignment of the cutting tool and the drive chuck.

18 Claims, 12 Drawing Sheets

Related U.S. Application Data continuation of application No. 15/018,990, filed on Feb. 9, 2016, now Pat. No. 10,080,579.

(60) Provisional application No. 62/138,331, filed on Mar. 25, 2015.

(51) Int. Cl.
*A61B 17/32* (2006.01)
*A61B 17/16* (2006.01)
*A61B 17/00* (2006.01)

(52) U.S. Cl.
CPC ........ *B23B 31/008* (2013.01); *B23B 31/1071* (2013.01); *A61B 2017/00398* (2013.01); *A61B 2017/00477* (2013.01); *B23B 2231/0244* (2013.01); *B23B 2231/0264* (2013.01); *B23B 2231/22* (2013.01)

(56) References Cited

U.S. PATENT DOCUMENTS

| | | | |
|---|---|---|---|
| 1,043,098 A | 11/1912 | Gross | |
| 1,053,709 A | 2/1913 | Collins | |
| 1,112,349 A | 9/1914 | Barnes | |
| 1,209,362 A | 12/1916 | Turner | |
| 1,539,439 A | 5/1925 | Smith | |
| 1,862,337 A | 6/1932 | Emrick | |
| 2,477,058 A | 7/1949 | Harborne et al. | |
| 2,512,033 A | 6/1950 | Metz | |
| 2,522,388 A | 9/1950 | Madsen | |
| 2,596,594 A | 5/1952 | Petre | |
| 2,682,184 A | 6/1954 | Szarkowski | |
| 2,726,872 A | 12/1955 | Onsrud | |
| 2,766,791 A | 10/1956 | Givens | |
| 2,773,693 A | 12/1956 | Chittenden | |
| 3,043,634 A | 7/1962 | Coley | |
| 3,136,347 A | 6/1964 | Linquist | |
| 3,589,826 A | 6/1971 | Fenn | |
| 3,637,225 A | 1/1972 | Schmuck | |
| 3,734,515 A * | 5/1973 | Dudek | B25B 23/0035 81/464 |
| 3,835,858 A | 9/1974 | Hagen | |
| 3,943,986 A | 3/1976 | Lejdegard | |
| 4,006,787 A * | 2/1977 | Rumpp | E21B 17/03 173/132 |
| 4,035,100 A | 7/1977 | Kruger et al. | |
| 4,047,722 A | 9/1977 | Nielsen et al. | |
| 4,078,593 A | 3/1978 | Benitz | |
| 4,107,949 A | 8/1978 | Wanner et al. | |
| 4,123,074 A | 10/1978 | Wanner | |
| 4,146,240 A | 3/1979 | Nielsen | |
| 4,185,383 A | 1/1980 | Heimke et al. | |
| 4,378,053 A | 3/1983 | Simpson | |
| 4,502,734 A | 3/1985 | Allen | |
| 4,512,692 A | 4/1985 | Nielsen et al. | |
| 4,565,472 A | 1/1986 | Brennsteiner et al. | |
| 4,594,036 A | 6/1986 | Hogenhout | |
| 4,632,195 A * | 12/1986 | Emmerich | E21B 17/046 403/383 |
| 4,655,651 A | 4/1987 | Hunger et al. | |
| 4,823,468 A | 4/1989 | Kollegger | |
| 4,830,000 A | 5/1989 | Shutt | |
| 4,917,274 A | 4/1990 | Asa et al. | |
| 5,009,440 A | 4/1991 | Manschitz | |
| 5,116,353 A | 5/1992 | Green | |
| 5,203,654 A | 4/1993 | Henderson | |
| 5,256,147 A | 10/1993 | Vidal et al. | |
| 5,263,786 A | 11/1993 | Kageyama | |
| 5,286,145 A | 2/1994 | Kleine | |
| 5,352,234 A | 10/1994 | Scott | |
| 5,382,249 A | 1/1995 | Fletcher | |
| 5,421,682 A | 6/1995 | Obermeier et al. | |
| 5,439,005 A | 8/1995 | Vaughn | |
| 5,466,101 A | 11/1995 | Meyen | |
| 5,487,626 A | 1/1996 | Von Holst et al. | |
| 5,499,985 A | 3/1996 | Hein et al. | |
| 5,505,737 A | 4/1996 | Gosselin et al. | |
| 5,549,634 A | 8/1996 | Scott et al. | |
| 5,569,256 A | 10/1996 | Vaughn et al. | |
| D377,982 S | 2/1997 | Walen | |
| 5,601,560 A | 2/1997 | del Rio | |
| 5,634,933 A | 6/1997 | Mccombs | |
| 5,697,158 A | 12/1997 | Klinzing et al. | |
| 5,720,749 A | 2/1998 | Rupp | |
| 5,735,535 A | 4/1998 | McCombs et al. | |
| 5,741,263 A | 4/1998 | Umber et al. | |
| 5,782,836 A | 7/1998 | Umber et al. | |
| 5,800,098 A * | 9/1998 | Satran | B23C 5/109 407/31 |
| 5,807,040 A | 9/1998 | Bongers-Ambrosius et al. | |
| 5,810,802 A | 9/1998 | Panescu et al. | |
| 5,833,704 A | 11/1998 | McCombs et al. | |
| 5,851,094 A | 12/1998 | Strand et al. | |
| 5,888,200 A | 3/1999 | Walen | |
| 5,893,851 A | 4/1999 | Umber et al. | |
| 5,928,241 A | 7/1999 | Menut | |
| 5,941,891 A | 8/1999 | Walen | |
| 5,964,555 A | 10/1999 | Strand | |
| 5,989,257 A | 11/1999 | Tidwell et al. | |
| 6,000,940 A | 12/1999 | Buss et al. | |
| 6,007,541 A | 12/1999 | Scott | |
| 6,012,881 A * | 1/2000 | Scheer | B23B 51/00 408/233 |
| 6,033,408 A | 3/2000 | Gage | |
| 6,062,575 A | 5/2000 | Mickel et al. | |
| 6,209,886 B1 | 4/2001 | Estes et al. | |
| 6,261,035 B1 | 7/2001 | Moores et al. | |
| 6,267,763 B1 | 7/2001 | Castro | |
| RE37,358 E | 9/2001 | del Rio | |
| 6,290,525 B1 | 9/2001 | Jacobi | |
| 6,409,221 B1 | 6/2002 | Robinson et al. | |
| 6,447,484 B1 | 9/2002 | Briscoe et al. | |
| 6,607,533 B2 | 8/2003 | Del Rio et al. | |
| 6,612,588 B2 | 9/2003 | Ostermeier et al. | |
| 6,688,610 B2 | 2/2004 | Huggins et al. | |
| 6,723,101 B2 | 4/2004 | Fletcher et al. | |
| 6,733,218 B2 | 5/2004 | Del Rio et al. | |
| D492,412 S | 6/2004 | Desoutter et al. | |
| 6,746,153 B2 | 6/2004 | Del Rio et al. | |
| 6,780,189 B2 | 8/2004 | Tidwell et al. | |
| 6,811,190 B1 | 11/2004 | Ray et al. | |
| 6,976,815 B2 | 12/2005 | Berglow | |
| 7,001,391 B2 | 2/2006 | Estes | |
| 7,011,661 B2 | 3/2006 | Riedel | |
| 7,066,940 B2 | 6/2006 | Riedel | |
| D536,791 S | 2/2007 | Eskridge et al. | |
| 7,261,169 B2 | 8/2007 | Kleine et al. | |
| 7,374,375 B2 | 5/2008 | Kleine et al. | |
| 7,429,154 B2 | 9/2008 | Kleine et al. | |
| 7,465,309 B2 | 12/2008 | Walen | |
| 7,488,327 B2 | 2/2009 | Rathbun et al. | |
| 7,497,860 B2 | 3/2009 | Carusillo et al. | |
| 7,549,992 B2 | 6/2009 | Shores et al. | |
| 7,559,927 B2 | 7/2009 | Shores | |
| D609,810 S | 2/2010 | Cote et al. | |
| 7,669,308 B2 | 3/2010 | Oshnock et al. | |
| 7,691,106 B2 | 4/2010 | Schenberger et al. | |
| 7,722,054 B2 | 5/2010 | Young | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| 7,766,585 B2 | 8/2010 | Vasudeva | |
| D631,962 S | 2/2011 | Dorman | |
| D636,082 S | 4/2011 | Cote et al. | |
| 7,922,720 B2 | 4/2011 | May et al. | |
| D641,468 S | 7/2011 | Ruiz et al. | |
| 8,043,292 B2 | 10/2011 | Carusillo | |
| D648,021 S | 11/2011 | Dorman | |
| D666,294 S | 8/2012 | Miles et al. | |
| 8,361,068 B2 | 1/2013 | McClurken | |
| 8,419,760 B2 | 4/2013 | Wiebe, III | |
| 8,518,065 B2 | 8/2013 | Shores et al. | |

(56) References Cited

U.S. PATENT DOCUMENTS

| | | |
|---|---|---|
| D692,134 S | 10/2013 | Lee-Sepsick |
| 8,597,316 B2 | 12/2013 | McCombs |
| 8,702,710 B2 | 4/2014 | Carusillo |
| 8,801,713 B2 | 8/2014 | del Rio |
| 8,893,820 B2 | 11/2014 | Barhitte et al. |
| D728,098 S | 4/2015 | Schad et al. |
| D728,099 S | 4/2015 | Schad et al. |
| D744,650 S | 12/2015 | Catron et al. |
| D746,457 S | 12/2015 | Swick et al. |
| D747,477 S | 1/2016 | Freigang et al. |
| D753,826 S | 4/2016 | Eggeling et al. |
| 9,333,561 B2 | 5/2016 | Nakai et al. |
| 9,597,737 B2 | 3/2017 | Hecht |
| 10,080,579 B2 | 9/2018 | Cihak |
| 10,314,610 B2 | 6/2019 | Dexter |
| 10,588,640 B2 | 3/2020 | Steinhauser |
| 10,849,634 B2 | 12/2020 | Nguyen |
| 2002/0105149 A1 | 8/2002 | Karst |
| 2002/0151902 A1 | 10/2002 | Riedel et al. |
| 2002/0171208 A1 | 11/2002 | Lechot et al. |
| 2003/0060841 A1 | 3/2003 | Del Rio |
| 2003/0097133 A1 | 5/2003 | Green et al. |
| 2003/0130663 A1 | 7/2003 | Walen |
| 2003/0140743 A1 | 7/2003 | Ofentavsek |
| 2003/0163134 A1 | 8/2003 | Riedel et al. |
| 2003/0229351 A1 | 12/2003 | Tidwell |
| 2005/0027282 A1 | 2/2005 | Schweikert et al. |
| 2005/0072007 A1 | 4/2005 | Proulx |
| 2005/0232715 A1 | 10/2005 | Baumann |
| 2006/0053974 A1 | 3/2006 | Blust |
| 2007/0172321 A1 | 7/2007 | Nagai |
| 2007/0282329 A1 | 12/2007 | Kawano |
| 2008/0033280 A1 | 2/2008 | Lubock et al. |
| 2009/0024129 A1 | 1/2009 | Gordon et al. |
| 2009/0312779 A1 | 12/2009 | Boykin et al. |
| 2010/0063524 A1 | 3/2010 | Mccombs |
| 2010/0076477 A1 | 3/2010 | Jezierski |
| 2011/0022069 A1 | 1/2011 | Mitusina |
| 2011/0190803 A1 | 8/2011 | To et al. |
| 2011/0218562 A1 | 9/2011 | Viola et al. |
| 2011/0238070 A1 | 9/2011 | Santangelo et al. |
| 2011/0270293 A1 | 11/2011 | Malla |
| 2011/0270294 A1 | 11/2011 | Rubin |
| 2012/0070220 A1 | 3/2012 | Ruiz et al. |
| 2012/0259336 A1 | 10/2012 | del Rio |
| 2012/0259337 A1 | 10/2012 | del Rio |
| 2013/0110147 A1 | 5/2013 | Dame |
| 2013/0116659 A1 | 5/2013 | Porter |
| 2013/0127123 A1* | 5/2013 | Miyanaga ............ B23B 31/008 408/226 |
| 2013/0138096 A1 | 5/2013 | Benn |
| 2013/0144267 A1 | 6/2013 | Chan et al. |
| 2013/0296848 A1 | 11/2013 | Allen, IV et al. |
| 2014/0056656 A1 | 2/2014 | Bae et al. |
| 2014/0124231 A1 | 5/2014 | Hessenberger et al. |
| 2014/0163558 A1 | 6/2014 | Cosgrove et al. |
| 2014/0303624 A1 | 10/2014 | del Rio et al. |
| 2014/0336654 A1 | 11/2014 | Pilgeram |
| 2014/0343454 A1 | 11/2014 | Miller et al. |
| 2014/0350561 A1 | 11/2014 | Dacosta et al. |
| 2014/0371752 A1 | 12/2014 | Anderson |
| 2016/0278788 A1 | 9/2016 | Dexter et al. |
| 2016/0278802 A1 | 9/2016 | Cihak |
| 2019/0388115 A1 | 12/2019 | Nguyen |
| 2020/0375612 A1 | 12/2020 | Nguyen |

FOREIGN PATENT DOCUMENTS

| | | | |
|---|---|---|---|
| CN | 103447599 A1 | 12/2013 | |
| CN | 103458805 A | 12/2013 | |
| DE | 8815261.8 | 3/1989 | |
| DE | 19846843 A1 * | 4/2000 | ........... B23B 31/008 |
| DE | 102012101259 | 8/2013 | |
| EP | 0293327 | 11/1988 | |
| EP | 1101459 B1 | 2/2006 | |
| EP | 1700655 A1 * | 9/2006 | ........... B23B 31/005 |
| EP | 1289714 B1 | 8/2008 | |
| EP | 1514034 B1 | 5/2011 | |
| FR | 1330849 | 6/1963 | |
| FR | 0216354 B1 | 7/1991 | |
| GB | 2129730 A | 5/1984 | |
| GB | 2491524 A | 12/2012 | |
| JP | 2014516611 A | 7/2014 | |
| RU | 2077275 C1 | 4/1997 | |
| WO | 9608343 | 3/1996 | |
| WO | 0166024 A1 | 9/2001 | |
| WO | 0189769 A1 | 11/2001 | |
| WO | 2007002230 A1 | 1/2007 | |
| WO | 2009012457 A1 | 1/2009 | |
| WO | 2012138337 A1 | 10/2012 | |
| WO | 2014037134 A1 | 3/2014 | |
| WO | 2014176060 A1 | 10/2014 | |

OTHER PUBLICATIONS

Korean Office Action 10-2017-7027832 dated Jan. 6, 2023 English Translation.

International Search Report and Written Opinion for International Application No. PCT/US2016/018686 dated Jul. 22, 2016 (17 pages).

International Search Report and Written Opinion for International Application No. PCT/US2019/031473 dated Aug. 19, 2019 (12 pages).

Product Catalog—vol. 9, Brasseler USA, Case 0:11-cv-01404-MJD-FLN Document 40-3 Filed Nov. 18, 2011—7 pgs.

* cited by examiner

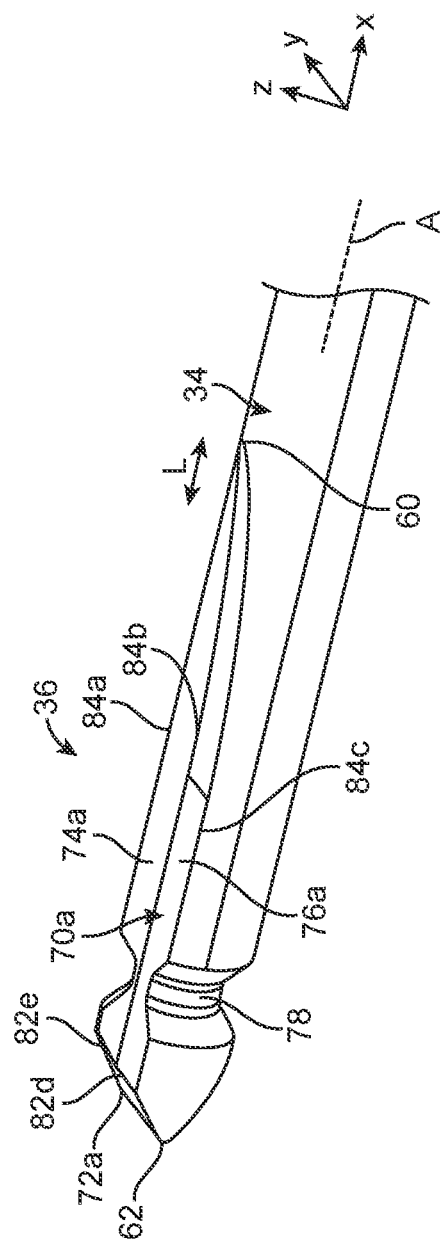
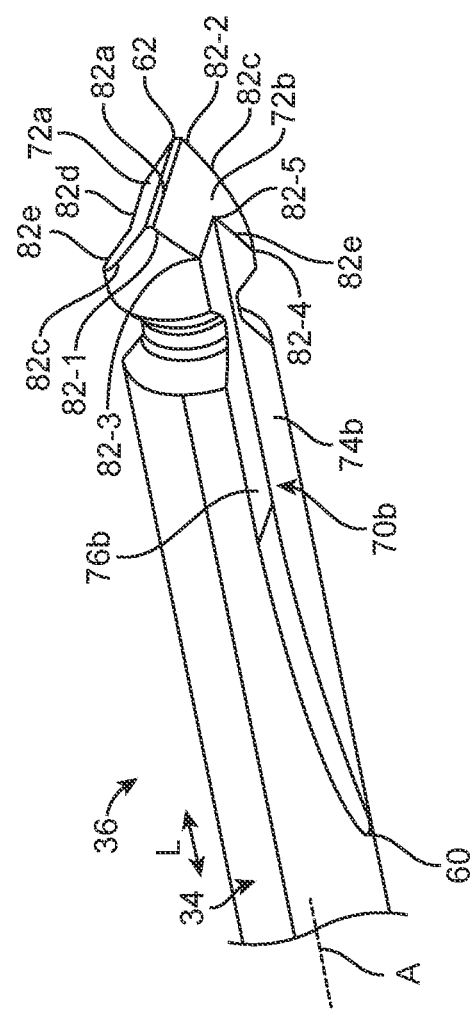
FIG. 4
FIG. 5

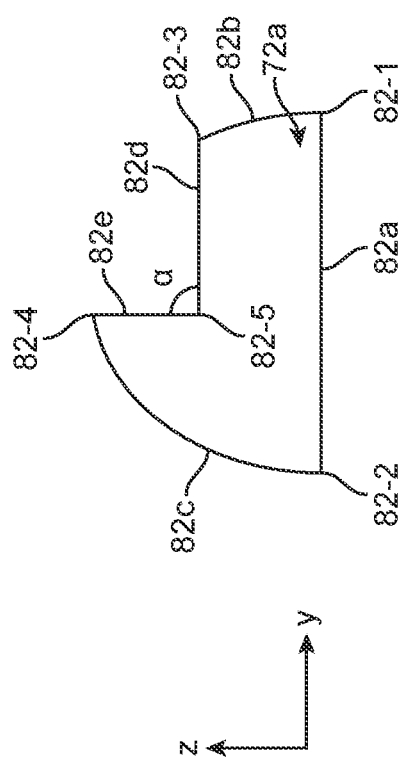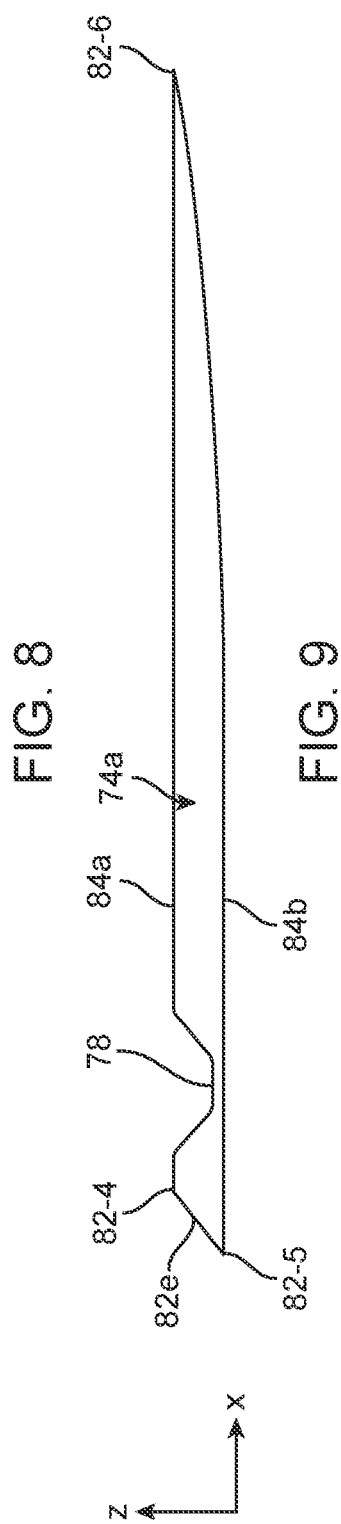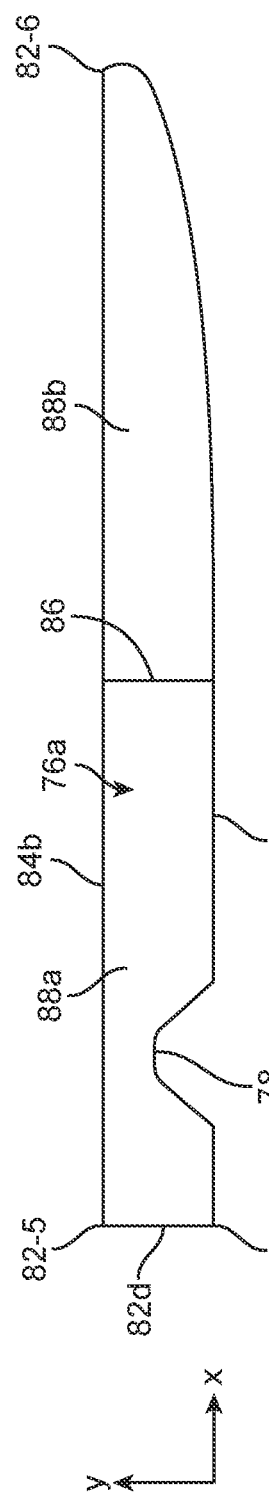

PIN DRIVE ROTARY SURGICAL CUTTING TOOLS AND POWERED HANDPIECES

CROSS REFERENCE TO RELATED APPLICATIONS

This is a Continuation Application of U.S. Non-Provisional patent application Ser. No. 16/106,597, filed Aug. 21, 2018, which is a continuation of U.S. Non-Provisional patent application Ser. No. 15/018,990, filed Feb. 9, 2016, now U.S. Pat. No. 10,080,579, which claims the benefit of the filing date of U.S. Provisional Patent Application Ser. No. 62/138,331, filed Mar. 25, 2015, all of which are herein incorporated by reference.

BACKGROUND

Concepts presented herein relate to rotary-type surgical cutting tools and powered handpieces. More particularly, it relates to rotary surgical cutting tools providing robust driven connection with a powered handpiece.

Powered surgical handpieces are commonly used in many medical specialties to drive surgical tools. For example, powered surgical handpieces are used to drive surgical drills, blades or other cutting tools in performing various diverse cutting-type functions including drilling, tapping, resection, dissection, debridement, shaving, pulverizing, and shaping of anatomical tissue including bone. The handpieces are typically configured for selective coupling to, and driving of, a variety of different rotary-type surgical cutting instruments that are each designed to perform a specific procedure. During use, based upon the specific surgical procedure, the surgeon selects the appropriate surgical tool and mounts it to the powered handpiece. The powered handpiece is then operated to move (e.g., rotation, oscillation) the tool in performing the surgical procedure. Additional procedural steps can later be performed by mounting a differently-styled tool to the same powered handpiece.

The improved capabilities of powered surgical handpieces, as well as the vast number of surgical cutting tools now available, have undoubtedly greatly increased the number of neurological, spine, ENT/head/neck and other procedures that a surgeon can perform utilizing a single surgical system (i.e., a single powered handpiece with multiple surgical cutting tools). Selective driven coupling between the powered handpiece and each tool is typically effectuated within a housing of the handpiece. The housing carries an internal drive chuck configured to receive a shank of the surgical cutting tool in a mating fashion. Thus, the shank of each surgical cutting tool useful with a particular handpiece has a common shape, with this shape corresponding to the handpiece drive chuck (e.g., circular, hexagonal). The drive chuck is connected to (or formed as part of) a drive shaft; upon connection of the surgical cutting tool to the drive chuck, powered rotation of the drive shaft rotates the cutting tool.

In current approaches, the cutting tool, including the shank, is generally shaped as an elongated cylinder defining a single central axis about which the tool is rotated during use. The handpiece drive chuck forms a corresponding, generally cylindrical-shaped passage for receiving the shank, effectuating a coupled connection and subsequent driven interface at point contacts created solely about the single central axis. The shank (or other regions of the cutting tool) may include recesses, grooves, or other features deviating from a truly cylindrical shape for purposes of effectuating an axial and/or rotational lock relative to the drive chuck. In some situations, complex machining/grinding can be required to achieve the requisite torque transmission and axial retention features, resulting in high contact stresses and reduced interface stiffness. These potential concerns, in turn, may lead to reliability issues, such as premature tool and/or handpiece failure. In other instances, alignment of the shank and drive chuck can be problematic, leading to user frustration.

SUMMARY

A surgical cutting tool includes an elongated shaft and a cutting head. The shaft defines a coupling portion terminating at a proximal end of the shaft, a stem portion, and a distal portion. The stem portion defines a central axis. The coupling portion defines an optional deflection surface positioned oblique with respect to the central axis and connected with at least one interface structure. The interface structure defines a first driven surface and a second driven surface. Upon insertion into a drive chuck, the deflection surface promotes self-alignment of the interface structure with a drive pin of the drive chuck.

As used throughout this disclosure, the term "edge" is in reference to an outside limit of an object, area or surface. Unless otherwise specifically noted, the term "edge" is not limited to a uniform, linear or straight line, and is inclusive of irregular, curved or complex shapes.

As used throughout this disclosure, the term "surface" is in reference to an outer part or extent of a body, having a continuous set of points that has length and breadth, but no thickness. Unless otherwise specifically noted, the term "surface" is not limited to a uniform, flat or planar face, and is inclusive of irregular, curved or complex shapes.

BRIEF DESCRIPTION OF THE DRAWINGS

FIG. 4 is an isometric view of a portion of a surgical cutting tool in accordance with principles of the present disclosure.

FIG. 5 is an isometric view of the surgical cutting tool of FIG. 4 from a different angle.

FIG. 8 is a plan view of a deflection surface portion of the surgical cutting tool of FIG. 4.

FIG. 9 is a plan view of a second driven surface of the surgical cutting tool of FIG. 4.

FIG. 10 is a plan view of primary first driven surface of the surgical cutting tool of FIG. 4.

DETAILED DESCRIPTION

Figure 1:
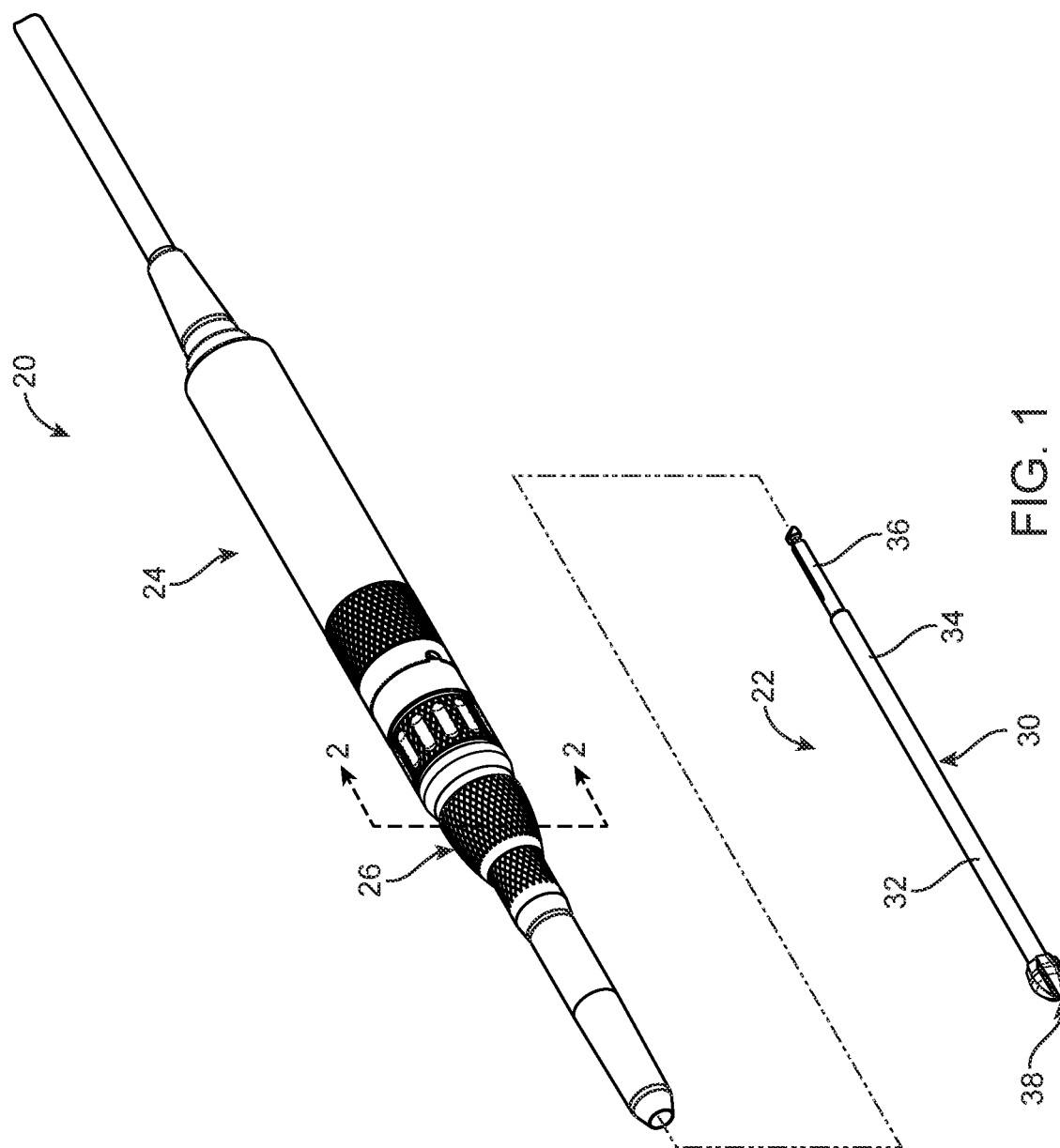
FIG. 1 is an exploded perspective view of a surgical cutting system.

One embodiment of a surgical cutting system 20 is shown in FIG. 1, and includes a rotary surgical cutting tool 22 and a powered handpiece 24. Details on the various components are described below. In general terms, the surgical cutting tool 22 is selectively coupled to the handpiece 24. Once mounted, the powered handpiece 24 is operated to rotate (e.g., rotate in a single direction or oscillate) the surgical cutting tool 22 in performing a desired surgical procedure. Aspects of the present disclosure are directed toward the coupling between the surgical cutting tool 22 and the powered handpiece 24, and in particular features provided with one or both of the surgical cutting tool 22 and the powered handpiece 24 that promote torque transmission onto the cutting tool 22 about an axis of the cutting tool 22. In some embodiments, concepts presented herein are embodied by the surgical cutting tool 22 alone; in other embodiments, concepts presented herein are embodied by the powered handpiece 24 alone; and in yet other embodiments, concepts presented herein are embodied by complimentary features provided with both of the surgical cutting tool 22 and the powered handpiece 24.

The powered handpiece 24 includes one or more features configured to interface with the surgical cutting tool 22 in selectively receiving/loading the surgical cutting tool and for rotatably driving a loaded surgical cutting tool. In this regard, the powered handpiece 24 can employ various drive assemblies or motors (e.g., pneumatically powered or driven, electrically powered or driven, etc.) as known in the art for effectuating driven rotation at desired speeds, and generally includes a housing assembly 26 maintaining a drive shaft (not shown) that mechanically couples or links a motor (not shown) to a drive chuck or collet via a coupling assembly. The drive chuck, in turn, is configured to receive the corresponding surgical cutting tool.

In some embodiments, the surgical cutting tool 22 includes or provides an elongated shaft 30. The shaft 30 can be formed of a rigid, surgically safe material (e.g., stainless steel), and defines a distal portion or region 32, an intermediate stem portion or region 34, and a proximal coupling portion or region 36. The distal portion 32 forms or carries (e.g., has assembled thereto) a cutting head 38. The cutting head 38 can assume a wide variety of forms appropriate for performing a desired rotary surgical cutting procedure (e.g., cutting, debulking, resecting, or removing anatomical tissue including bone). By way of one non-limiting embodiment, the cutting head 38 can be a bur having any shape, size, flute pattern, etc., as desired. While the elongated shaft 30 is illustrated as being linear or straight, in other embodiments the shaft 30 can define one or more longitudinal bends or curves; in related embodiments, surgical cutting tools of the present disclosure can further include an outer sleeve (not shown) that supports a curved version of the shaft 30 as the shaft 30 is rotated.

Figure 2:
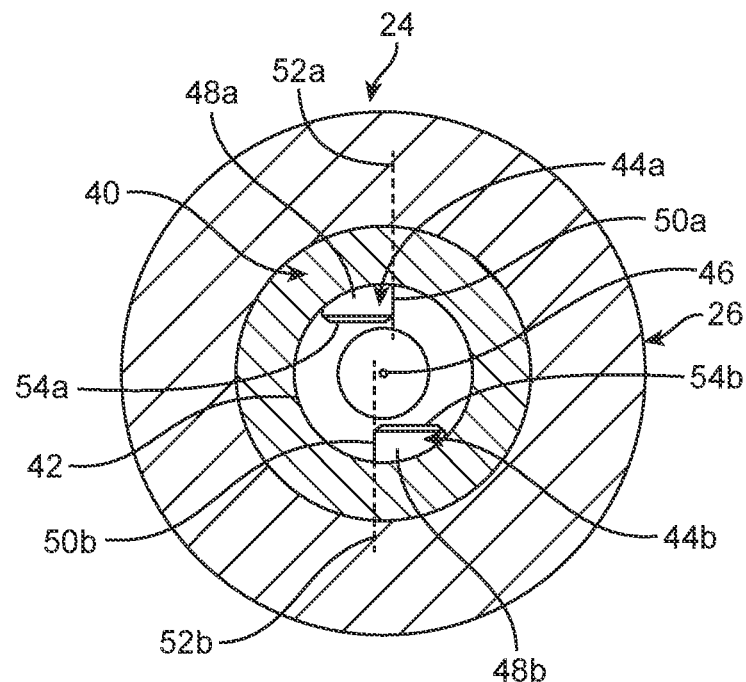
FIG. 2 is a sectional view of a powered handpiece taken along the line 2-2 in FIG. 1.
Figure 3:
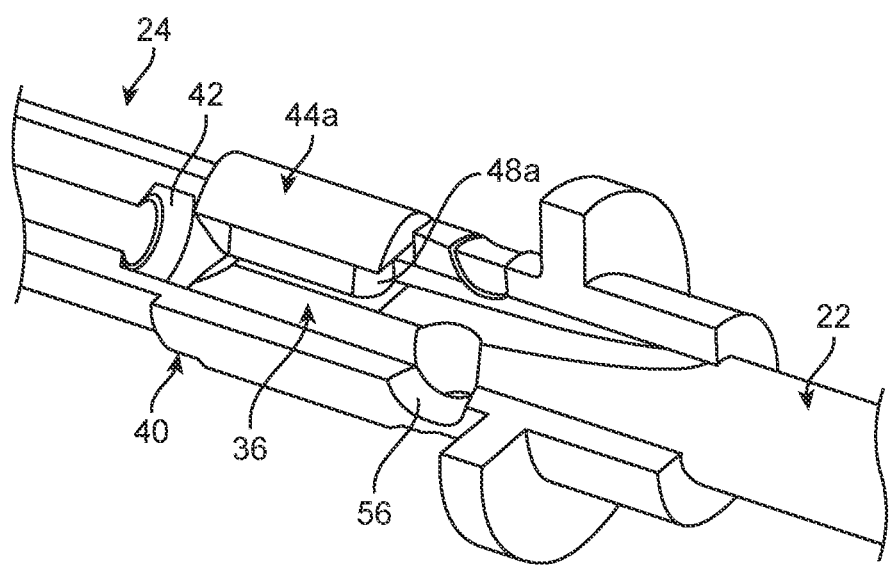
FIG. 3 is an isometric view of a drive chuck and a surgical tool seated within the drive chuck.

FIG. 2 is a schematic sectional view of the handpiece 24 taken along the line 2-2 in FIG. 1 and FIG. 3 is a partial isometric view of the cutting tool 22 seated within the handpiece 24. As illustrated, the handpiece 24 includes a drive chuck 40 that defines an interior passage 42 sized to receive the cutting tool 22. The drive chuck 40 has an elongated shape, and is generally configured for mounted assembly to a drive shaft (not shown) component of the powered handpiece 24 (FIG. 1) in a manner that creates a rigid coupling there between. Any other coupling assembly construction is equally acceptable. In yet other embodiments, the drive chuck 40 and the drive shaft can be integrally formed as a single, homogenous part.

A diameter of the passageway 42 can be selected so as have a diameter slightly greater than an outer diameter of the cutting tool 22. The drive chuck 40 further includes opposed drive pins or drive bodies 44a, 44b configured to interface with the cutting tool 22, as discussed below. During operation of the powered handpiece 24, the drive chuck 40 rotates drive pins 44a, 44b about a rotational axis 46 of the handpiece 24. In some embodiments, the drive pins 44a, 44b can be formed separately from and assembled to a remainder of the drive chuck 40 as reflected by FIGS. 2 and 3; in other embodiments described elsewhere, the drive pins or bodies 44a, 44b are integrally formed by the drive chuck 40.

Each of the pins 44a and 44b defines a leading end 48a, 48b, a first drive surface 54a, 54b, and a second drive surface 50a, 50b. In one embodiment, as discussed in more detail below, the leading ends 48a, 48b can be curved or arcuate in shape so as to encourage rotational alignment of the coupling portion 36 of the cutting tool 22 with the drive pins 44a, 44b. The second drive surfaces 50a, 50b, in the embodiment illustrated, are offset with respect to the rotational axis 46 and with respect to one another. For example, a plane 52a defined by the second drive surface 50a of the first drive pin 44a does not intersect with the rotational axis 46 or with a corresponding plane 52b defined by the second drive surface 50b of the second drive pin 44b. In other embodiments, arrangement of the second drive surfaces 50a, 50b can be selected such that one or both of planes 52a, 52b intersect with the rotational axis 46. Regardless, the second drive surfaces 50a, 50b can serve to locate or align respective surfaces of the cutting tool 22 with the drive pins 44a, 44b and/or to transfer torque on to the cutting tool 22.

In additional embodiments, it will be appreciated that only a single drive pin or drive body can be used as well as three or more drive pins as desired. In any event, rotation of the chuck 40 in a first or primary rotational direction (e.g., counterclockwise relative to the orientation of FIG. 2) causes the first drive surfaces 54a, 54b to serve as surfaces that drive rotation of the tool 22. When rotating in an opposite or secondary direction (e.g., clockwise relative to the orientation of FIG. 2), the second drive surfaces 50a, 50b serve to drive rotation of the tool 22. It will be appreciated that the terms "primary" and "secondary" are illustrative in that the terms serve to differentiate between adjacent or connected drive surfaces. In this manner, the terms can be interchangeable.

As illustrated in FIG. 3, the first drive pin 44a is engaged with the coupling portion 36. In addition to the first drive pin 44a, the handpiece 24 can optionally include or define one or more axial retention features that serve to effectuate an axial "lock" of the tool 22 when fully inserted into the powered handpiece 24. The axial retention feature, where provided, can assume various forms and is typically designed in tandem with corresponding components provided with the cutting tool 22. For example, in the exemplary embodiment of FIG. 3, an axial retention feature (e.g., a ball—not shown) is provided in an opening 56 that can engage a corresponding feature on the cutting tool 22. The axial retention feature can alternatively be one or more mechanisms to engage the cutting tool 22. In yet other embodiments, the axial retention feature can be omitted.

One embodiment of the coupling portion 36 is shown in greater detail in FIGS. 4-7, along with a portion of the intermediate stem portion 34. As a point of reference, the elongated shape of the shaft 30 serves to generate a longitudinal or length direction "L", based upon which other geometry features can be identified. For ease of understanding, x, y, and z conventions are provided with the views; the x direction or axis corresponds with the longitudinal or length direction L. The coupling portion 36 extends proximally in the length direction L from a first location generally indicated at 60, and terminates at a second location 62 or proximal end of the shaft 30. In some non-limiting embodiments, the proximal end 62 can be viewed as defining a surface or edge perpendicular to the central axis A and perpendicular to the plan view of FIG. 7. At least a majority of an overall length of the shaft 30 is defined along the intermediate stem region 34 (e.g., the length of the intermediate stem portion 34 is at least five times the length of the coupling portion 36), with a shape of the intermediate stem portion 34 defining a central axis A of the shaft 30. For example, the intermediate stem portion 34 can be cylindrical (e.g., an elongated right cylinder), cylindrical-like, or have any other constant shape along at least a majority of a length of the intermediate stem portion 34 in a form that otherwise generates the central axis A.

Figure 6:
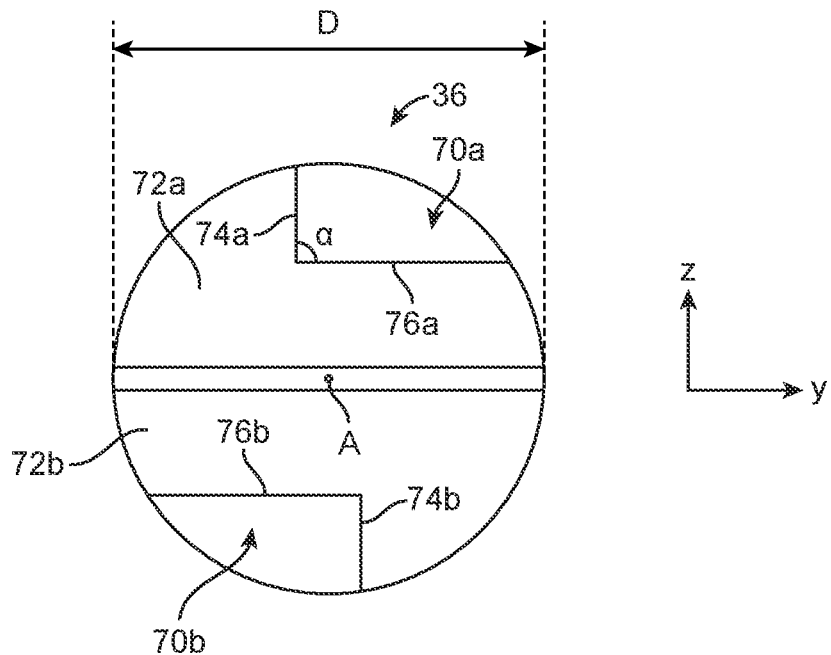
FIG. 6 is a plan view of a proximal end of the surgical cutting tool of FIG. 4.
Figure 7:
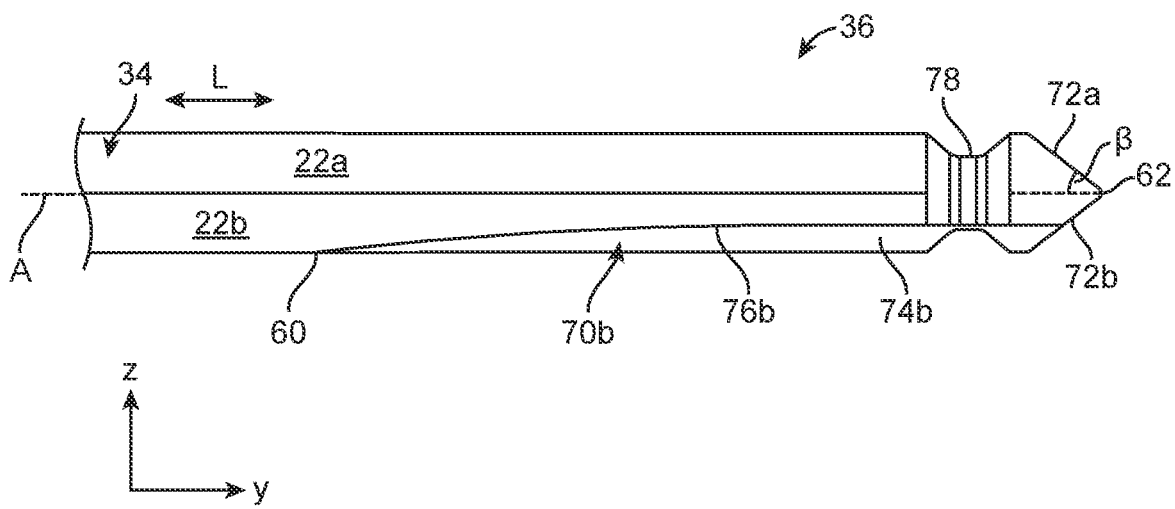
FIG. 7 is a plan view of a side of the surgical cutting tool of FIG. 4.

A shape of the intermediate stem region 34 can be viewed as defining a maximum outer dimension (e.g., diameter) D (FIG. 6) in a plane perpendicular to the central axis A and length direction L (i.e., a plane parallel to the view of FIG. 6). The central axis A can intersect a center point of the maximum outer dimension D. While the shape of the intermediate stem portion 34 is reflected as being a circle (e.g., the intermediate stem portion 34 is an elongated right cylinder), the intermediate stem portion 34 can have other cross-sectional shapes that establish the maximum outer dimension D and that that may not be truly circular in nature. In some embodiments, surface features can optionally be incorporated into the intermediate stem portion 34 such that an entirety of the intermediate stem portion 34 need not necessarily have a constant or uniform shape; however, a cross-sectional shape of the intermediate stem portion 34 along at least a majority of the longitudinal length L generates the central axis A. The cutting head 38 (FIG. 1) can be configured to effectuate desired tissue removal when revolved about the major central axis A. For example, a shape or other features of the cutting head 38 can be concentric or centered about the major central axis A.

With the above definitions in mind, extension of the coupling portion 36 relative to the intermediate stem portion 34 in the length direction L (or x direction) is configured for establishing a driven interface with the handpiece 24 (FIG. 1). The coupling portion 36 can be sized and shaped to interface with the drive chuck 40 and pins 44a, 44b (FIGS. 2 and 3) of the handpiece 24 in various manners as described below. In general terms, however, the coupling portion 36 serves to transfer torque from the handpiece 24 to the cutting tool 22, in which a drive or input torque provided by the drive chuck 40 through the pins 44a, 44b to the coupling portion 36 is transferred to the intermediate stem portion 34, and thus a remainder of the cutting tool 22, as a torque about the central axis A. To this end, the coupling portion 36 forms or includes first and second interface structures 70a, 70b that provide torque transfer by engaging the input torque from the motor of the powered handpiece 24. In particular, the first interface structure 70a is configured to engage a first one of the drive pins 44a, 44b, whereas the second interface structure 70b is configured to simultaneously engage the other of the drive pins 44a, 44b. With this configuration, the cutting tool 22 allows increased torque transfer as compared to conventional rotary-type cutting tools. In some embodiments, the cutting tools of the present disclosure form or include exactly two of the interface structures (e.g., the interface structures 70a, 70b). In alternative embodiments, the coupling portion 36 can include only a single interface structure or three or more interface structures as desired.

In some embodiments, the interface structures 70a, 70b can be viewed as slots or cut-outs in an otherwise uniform shape of the shaft 30. For example, FIGS. 4-6 reflect that a majority of the shaft 30 can have a right cylinder shape in some non-limiting embodiments; the interface structures 70a, 70b can be slots or cut-outs formed into the right cylinder shape. The first interface structure 70a can be defined as extending from an optional deflection surface 72a, and includes or provides a first or primary driven surface 76a and a second or secondary driven surface 74a. In a like manner, the second interface structure 70b extends from an optional deflection surface 72b, and includes or provides a first or primary driven surface 76b, and a second or secondary driven surface 74b. Details for each of the surfaces are provided below. In general, however, the optional deflection surfaces 72a, 72b are each provided to assist in facilitating rotational alignment of the cutting tool 22 with the drive pins 44a, 44b during insertion of the tool 22 within the handpiece 24. In particular, the deflection surfaces 72a, 72b can engage a respective one of the leading ends 48a, 48b of the drive pins 44a, 44b. Once aligned and seated, the interface structures 70a, 70b provide a driven interface with the drive pins 44a, 44b.

The second driven surfaces 74a, 74b of the interface structures 70a, 70b are configured to engage a corresponding one of the second drive surfaces 50a, 50b of the drive pins 44a, 44b. To this end, the second driven surfaces 74a, 74b can be defined as being offset with respect to one another and with respect to the central axis A. Furthermore, the first driven surfaces 76a, 76b locate the second driven surfaces 74a, 74b with respect to the corresponding first drive surfaces 56a, 56b on the drive pins 44a, 44b. In locating the second driven surfaces 74a, 74b to be offset from the central axis A as illustrated in FIG. 6, the first driven surfaces 76a, 76b extend from the outer dimension D of the tool 22 and cross a central plane perpendicular to and including the central axis A (extending perpendicular to the view of FIG. 6), where the first driven surfaces 76a, 76b connect with the second driven surfaces 74a, 74b.

Each of the interface structures 70a, 70b can be defined as being positioned within a particular half of the cutting tool 22. For instance, with reference to FIG. 7, a central plane of the tool 22 can be defined by the central axis A and a line parallel with the proximal end 62 (i.e., the central plane is a plane of the x, y axes and includes the central axis A). First and second halves 22a, 22b are defined at opposite sides (i.e., in opposite directions along the z axis) of the central plane. In some embodiments, the first interface structure 70a can be defined as being entirely positioned within the first half 22a, with the second interface structure 70b being entirely positioned within the second half 22b. In other embodiments, modifications of the interface structures 70a, 70b can be made consistent with concepts presented herein. For example, one of the deflection surfaces 72a, 72b can be eliminated wherein the other deflection surface provides self-alignment of the cutting tool 22 as discussed below. In still further embodiments, only a single interface structure 70a, 70b is utilized, wherein the other interface structure is eliminated, for example when utilized with a drive chuck employing a single pin drive. In yet other embodiments, the interface structures 70a, 70b need not be confined to a particular half of the cutting tool 22 and can be positioned within both halves of the cutting tool 22, as desired.

As alluded to above, the surgical cutting tool 22 can optionally include or define one or more axial retention features that serve to effectuate an axial "lock" of the tool 22 when fully inserted into the powered handpiece 24 (FIG. 1). The axial retention feature, where provided, can assume various forms and is typically designed in tandem with corresponding components provided with the powered handpiece 24. For example, in the exemplary embodiment illustrated, an axial retention feature is provided as a circumferential groove 78. The groove 78 is formed distally away from the deflection surfaces 72a, 72b and such that it interrupts the second driven surfaces 74a, 74b and the first driven surfaces 76a, 76b. Alternatively, the groove 78 (or other retention feature) can be located elsewhere along the coupling portion 36. Alternatively, the feature can be located in the intermediate stem portion 34. The axial retention feature can alternatively be one or more notches, flats, holes, troughs, a biased mechanism, etc. In yet other embodiments, the axial retention feature can be omitted.

In some embodiments, the deflection surfaces 72a, 72b can be identical, such that the following description of the deflection surface 72a of the first interface structure 70a is applicable to the deflection surface 72b of the second interface structure 70b. With further reference to FIG. 8, the deflection surface 72a is bound by a leading edge 82a, first and second side edges 82b, 82c, and first and second intermediate or interposing connecting edges 82d, 82e. In the illustrated, non-limiting embodiment, the leading edge 82a is positioned at the proximal end 62 (FIG. 7) of the tool 22 and extends perpendicular to both the central axis A and to the length direction L. In particular, the leading edge 82a extends in the y direction from a first terminal point 82-1 to a second terminal point 82-2. While the leading edge 82a is shown as being substantially linear (i.e., within 5% of a truly linear shape), other shapes, such as curved, complex, irregular, etc., are also acceptable. On either side of the leading edge 82a, the first and second side edges 82b, 82c extend away from the corresponding terminal point 82-1, 82-2. In particular, the first side edge 82b extends from the first terminal point 82-1 to a third terminal point 82-3, whereas the second side edge 82c extends from the second terminal point 82-2 to a fourth terminal point 82-4. Extension of the first side edge 82b from the first terminal point 82-1 to the third terminal point 82-3 includes a component in the x direction (i.e., into the plane of FIG. 8), and optionally can be curved in the y and z directions (e.g., a radius of curvature of the first side edge 82b reflected by the y, z plane view of FIG. 8 corresponds with a radius of curvature of the tool 22 along the intermediate stem portion 34). Similarly, extension of the second side edge 82c from the second terminal point 82-2 to the fourth terminal point 82-4 includes a component in the x direction, and optionally can be curved in the y and z directions (e.g., a radius of curvature reflected by the y, z plane view of FIG. 8 corresponds with a radius of curvature of the tool 22 along the intermediate stem portion 34). Other shapes are also envisioned. In more general terms, and as best reflected in FIG. 5 for the corresponding side edges 82b, 82c of the deflection surface 72b of the second interface structure 70b, the side edges 82b, 82c have an x direction component (i.e., are not perpendicular to the central axis A) in extension between the corresponding terminal points 82-1, 82-3 and 82-2, 82-4, respectively.

Returning to FIGS. 4 and 8, the first and second connecting edges 82d, 82e generally correspond with a respective one of the driven surfaces 74a, 76a, rendering the first deflection surface 72a "open" to the first interface structure 70a in the longitudinal or length direction L (e.g., as explained in greater detail below, a body (such as one of the drive pins 44a, 44b) can pass "through" the deflection surface 72a and into or out of engagement with the driven surfaces 74a, 76a of the first interface structure 70a via the first and second connecting edges 82d, 82e). For example, FIG. 4 reflects geometry of the first connecting edge 82d corresponding with the first driven surface 76a, and geometry of the second connecting edge 82e corresponding with the second driven surface 74a. The first connecting edge 82d extends from the first side edge 82b toward the central axis A and, in the embodiment illustrated, can be parallel with the leading edge 82a. In particular, the first connecting edge 82d extends from the third terminal point 82-3 to a fifth terminal point 82-5. The second connecting edge 82e extends from the second side edge 82c in a direction toward the central axis A and intersects with the first connecting edge 82d at the fifth terminal point 82-5. An angle α defined by the first and second connecting edges 82d, 82e corresponds with a geometry relationship of the first and second driven surfaces 74a, 74b, and can be 90 degrees. In other embodiments, the angle α can be in a range from 75 degrees to 105 degrees, as desired.

The deflection surface 72a is reflected in several of the views as optionally being planar, although in other embodiments the deflection surface 72a can be arcuate or define other shapes (uniform, regular, irregular, etc.) as desired such that the deflection surface 72a may not be truly planar in nature. In some embodiments, surface features can optionally be incorporated into the deflection surface 72a such that an entirety of the deflection 72a need not necessarily have a constant or uniform shape. However, a major plane of the deflection surface 72a generally extends in a direction that is oblique to the central axis A. In particular, a shape of the deflection surface 72a can be defined as defining a major plane extending at an angle β (FIG. 7) with respect to the central axis A. In some embodiments, the angle β is approximately 45 degrees, wherein in other embodiments, the angle β is in a range from approximately 10 to 70 degrees, alternatively in a range from 30 degrees to 60 degrees, or other ranges as desired.

With reference to FIGS. 4, 5 and 9, the second driven surfaces 74a, 74b can be identical in some embodiments, such that the following description of the second driven surface 74a of the first interface structure 70a applies equally to the second driven surface 74b of the second interface structure 70b. The second driven surface 74a is bound by the second connecting edge 82e, a first outer longitudinal edge 84a and an inner longitudinal connecting edge 84b. The second driven surface 74a is reflected as being planar, although in other embodiments the second driven surface 74a can be arcuate or can define other shapes (regular or irregular) as desired such that second driven surface 74a may not be truly planar in nature. In some embodiments, surface features can optionally be incorporated into the second driven surface 74a such that an entirety of the second driven surface 74a need not necessarily have a constant or uniform shape. However, the second driven surface 74a generally extends between the longitudinal edges 84a, 84b in a direction that is perpendicular to the central axis A. The outer longitudinal edge 84a extends from the fourth terminal point 82-4 to a sixth terminal point 82-6 and is located at the maximum outer dimension D (FIG. 6). In one embodiment and as illustrated, the outer longitudinal edge 84a extends parallel to the central axis A. Where provided, the outer longitudinal edge 84a is interrupted by the circumferential groove 78. The inner longitudinal connecting edge 84b extends from the fifth terminal point 82-5 to the sixth terminal point 82-6 in some embodiments. To this end, the inner longitudinal edge 84b can taper with respect to the central axis A along the length direction L. Other shapes are also acceptable, and can generally correspond with geometry of the first driven surface 76a as described below.

With reference to FIGS. 4, 5, and 10, the first driven surfaces 76a, 76b can be identical in some embodiments, such that the following description of the first driven surface 76a of the first interface structure 70a applies equally to the first driven surface 76b of the second interface structure 70b. The first driven surface 76a is bound by the first connecting edge 82d, a second outer longitudinal edge 84c and the inner longitudinal connecting edge 84b. The first driven surface 76a is reflected as being curvilinear (best reflected in FIGS. 4 and 5), although in other embodiments the first driven surface 76a can be entirely planar or define other shapes (regular or irregular) as desired such that the first driven surface 76a may not conform to a single curve or curves in nature. In some embodiments, surface features can optionally be incorporated into the first driven surface 76a such that an entirety of the first driven surface 76a need not necessarily have a constant or uniform shape. The second outer longitudinal edge 84c extends from the third terminal point 82-3 to the sixth terminal point 82-6 and is located at the maximum outer dimension D (FIG. 6). Where provided, the circumferential groove 78 interrupts the second outer longitudinal edge 84c.

As a point of reference, the shape of the first driven surface 76a as reflected by FIG. 10 can, in some embodiments, result from or be a function of a selected manufacturing process (e.g., a milling or cutting process in which the first interface structure 70a is cut into a right cylinder rod) and is in no way limiting. With some optional manufacturing processes, for example, the first interface structure 70a is formed by a cutting wheel operated to initiate cutting at the proximal end 62 (FIG. 7) and proceeding in the distal direction to simultaneously generate the first and second driven surfaces 76a, 74a. With these and similar techniques, the rotating cutting wheel and the rod being cut are manipulated relative to one another so as to form relatively flat or planar cut surfaces of sufficient surface area for the driven surfaces 74a, 76a. Once flat surfaces of sufficient surface area are established, the cutting wheel is removed from the rod being cut; due to the circular nature of the cutting wheel, "outrun" is formed into the rod being cut beyond the relatively flat or planar cut surfaces (with the "outrun" or curvature being commensurate with a diameter of the cutting wheel). FIG. 10, for example, reflects a hypothetical transition line 86 along a length of the first driven surface 76a, with first and second portions 88a, 88b being defined at opposite sides of the transition line 86. The transition line 86 represents a location of a centerline of the cutting tool when withdrawn from a thickness of the material being cut after forming the first portion 88a. The first portion 88a serves as the area of expected engaged interface with one of the drive pins 44a, 44b (FIG. 2). In some embodiments, then, the first portion 88a of the first driven surface 76a can be substantially planar (i.e., within 5% of truly planar or flat surface). The second portion 88b is not intended to necessarily directly interface with the drive pins 44a, 44b, and instead can be generated by the selected manufacturing technique (e.g., outrun). The curved nature of the second outer longitudinal edge 84c along the second portion 88b in the planar view of FIG. 10 results from a diameter or outrun of the cutting wheel; FIG. 4 illustrates this same effect, with the "curve" (as in FIG. 10) of the second outer longitudinal edge 84c along the second portion 88b being a function of the right cylinder shape. With additional reference to FIG. 9, the second driven surface 74a can include this same ease of manufacture effect, with the tapering nature of the inner connecting edge 84b (described above) resulting from a diameter or outrun of the cutting wheel (i.e., the tapering or curved shape of the inner connecting edge 84b initiates at location corresponding with the hypothetical transition line 86 described above).

Returning to FIGS. 1-3, prior to operation, a user inserts the cutting tool 22 into the powered handpiece 24. The complementary configuration of the coupling portion 36 of the cutting tool 22 and the drive chuck 40 (including the drive pins 44a, 44b) of the powered handpiece 24 is such that automatic, rotational self-alignment of the cutting tool 22 with the drive chuck 40 is achieved upon insertion of the tool 22 into the handpiece 24. In particular, insertion of the surgical cutting tool 22 into the drive chuck 40 will be described with respect to FIGS. 11 and 12a-c. It will be understood that the powered handpiece 24 (FIG. 1) can include multiple other components that interface with the surgical cutting tool 22 and/or support the drive chuck 40 (and other components mounted to the drive chuck 40, such as a drive shaft). For ease of understanding, the views of FIGS. 11 and 12a-c illustrate the drive pins 44a, 44b of the drive chuck 40 and the surgical cutting tool 22 in isolation.

Figure 11:
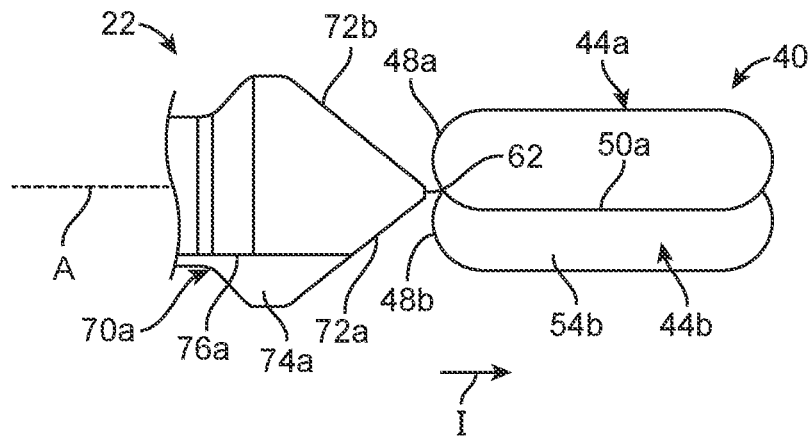
FIG. 11 is a schematic top view of insertion of a surgical cutting tool into a drive chuck.
Figures 12A, 12B:
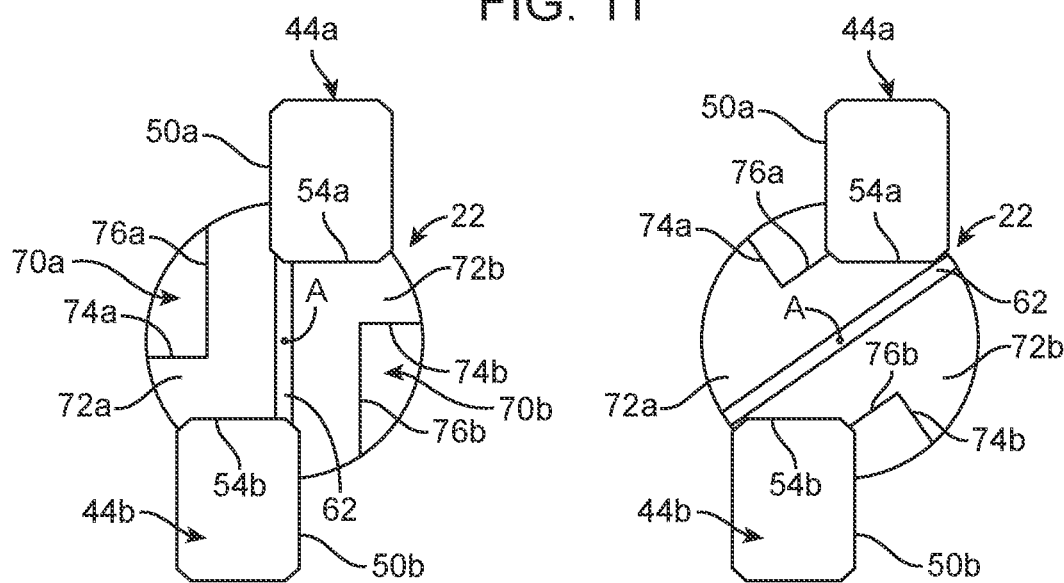
FIGS. 12A-12C are schematic plan views of different rotational positions for a surgical cutting tool being inserted into a drive chuck.

In the schematic illustration of FIGS. 11 and 12a, the surgical cutting tool 22 is poised for insertion relative to the drive pins 44a, 44b of the drive chuck 40. In most scenarios, the interface structures 70a, 70b will not be precisely aligned with the drive pins 44a, 44b upon initial insertion. However, the oblique angle of the deflection surfaces 72a, 72b relative to the central axis A promotes self-alignment of the interface structures 70a, 70b as the surgical cutting tool 22 is inserted into the drive chuck 40. Even if the interface structures 70a, 70b are misaligned relative to the drive pins 44a, 44b, the deflection surfaces 72a, 72b will come into sliding contact with the leading ends 48a, 48b of the drive pins 44a, 44b. This sliding interface has a cam-like effect, causing the surgical cutting tool 22 to rotate with further insertion and bringing the interface structures 70a, 70b into alignment with a corresponding one of the drive pins 44a, 44b. In particular, the deflection surfaces 72a, 72b are configured to engage the leading ends 48a, 48b of the drive pins 44a, 44b upon initial insertion in the event the interface structures 70a, 70b are not rotationally aligned with the drive pins 44a, 44b.

In order to promote self-alignment, an angle between the deflection surfaces 72a, 72b can be selected such that the proximal end 62 is sized to fit between the first drive surfaces 54a, 54b of the drive pins 44a, 44b. Moreover, a distance between the first driven surfaces 76a, 76b of the tool 22 can be selected to be equal to or greater than a distance between the first drive surfaces 54a, 54b of the drive pins 44a, 44b. In addition, a location of the second driven surfaces 74a, 74b of the tool 22 are selected to correspond with an offset of the second drive surfaces 50a, 50b of the drive pins 44a, 44b. In any event, when seating the cutting tool 22 within the drive chuck 40, the second driven surface 74a of the first interface structure 70a is brought into alignment with the second drive surface 50a of the first drive pin 44a or with the second drive surface 50b of the second drive pin 44b due to a symmetrical construction of the cutting tool 22.

In FIGS. 11 and 12a, the second driven surface 74a of the first interface structure 70a has been randomly arranged upon initial insertion to be perpendicular to the second drive surface 50a of the first drive pin 44a. As such, the tool 22 needs to be rotated (e.g., approximately 90 degrees) in order to align the first interface structure 70a with the first drive pin 44a and the second interface structure 70b with the second drive pin 44b (e.g., the first and second driven surfaces 76a, 74a of the first interface structure 70a are not aligned with the corresponding first and second drive surfaces 54a, 50a of the first drive pin 44a). As the surgical cutting tool 22 is moved toward the drive pins 44a, 44b in a direction of arrow I in FIG. 11 (e.g., indicating an insertion force), the deflection surfaces 72a, 72b contact the leading ends 48a, 48b.

Figure 12C:
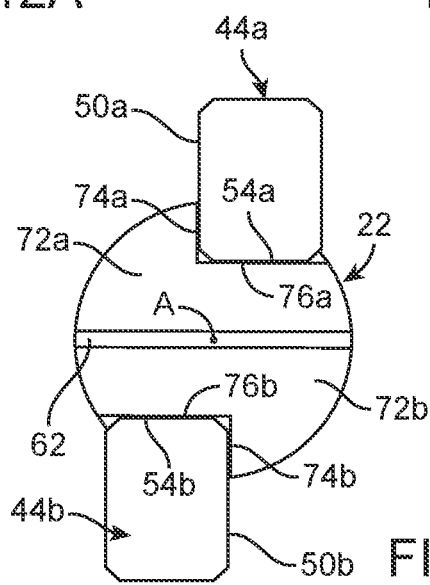

As insertion continues, FIGS. 12a-c illustrate rotational alignment between the cutting tool 22 and the drive pins 44a, 44b. Upon further insertion and as illustrated in FIG. 12b, the insertion force causes contact between the deflection surfaces 72a, 72b and the leading ends 48a, 48b, respectively. Due to the angle of the deflection surfaces 72a, 72b, the cutting tool 22 begins to rotate such that the interface structures 70a, 70b approach rotational alignment with the drive pins 44a, 44b. Upon yet further insertion, the deflection surfaces 72a, 72b interact with the leading ends 48a, 48b to effectuate further rotation of the cutting tool 22 about central axis A. As illustrated in FIG. 12c, when the interface structures 70a, 70b are brought into alignment with a respective one of the drive pins 44a, 44b, continued application of the insertion force I results in the drive pins 44a, 44b traveling along the so-aligned interface structures 70a, 70b. For example, and as further illustrated in FIGS. 3 and 12c, rotational alignment between the tool 22 and the drive pins 44a, 44b (as dictated by an interface between the deflection surfaces 72a, 72b and the drive pins 44a, 44b as described above) can include the second drive surface 50a of the first drive pin 44a aligned with second driven surface 74a of the first interface structure 70a, as well as the first drive surface 54a of the first drive pin 44a being aligned with the first driven surface 76a of the first interface structure 70a. In a similar manner, the first and second drive surfaces 74b, 76b of the second drive pin 44b are aligned with the first and second driven surfaces 76a, 74a, respectively, of the second interface structure 70b.

Figure 13:
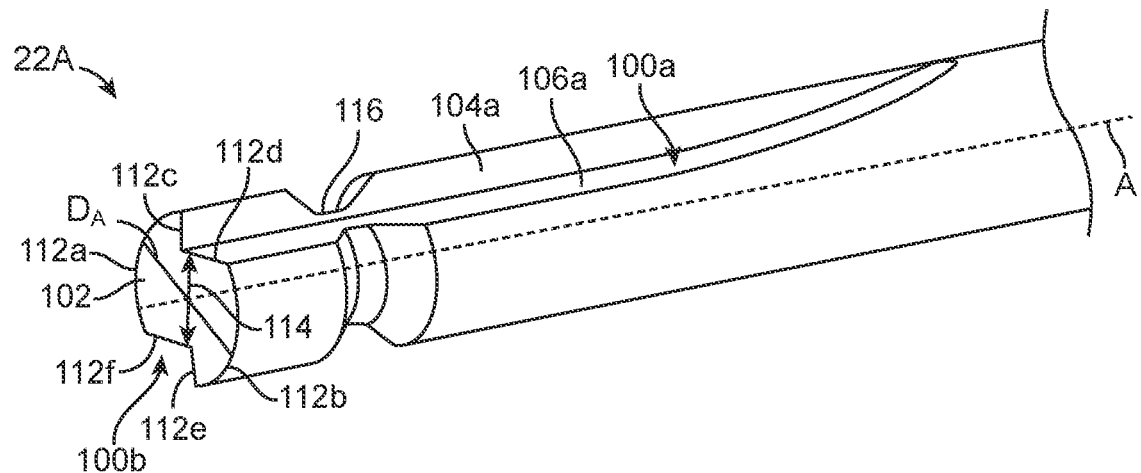
FIG. 13 is an isometric view of a portion of another surgical cutting tool in accordance with principles of the present disclosure.
Figure 14:
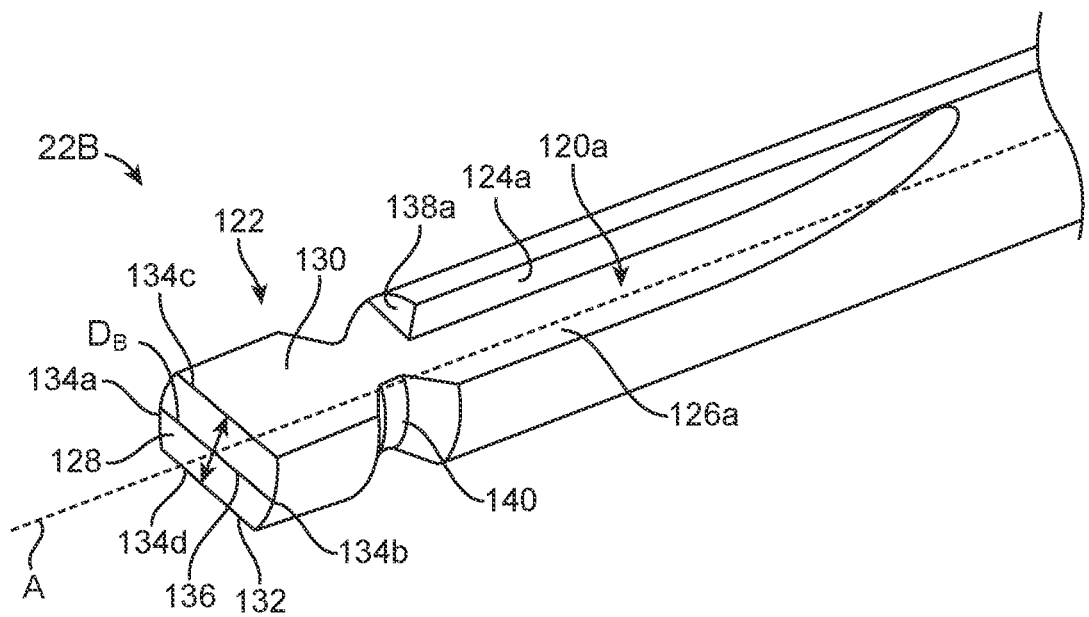
FIG. 14 is an isometric view of a portion of another surgical cutting tool in accordance with principles of the present disclosure.

In other embodiments of surgical cutting tools of the present disclosure, one or both of the deflection surfaces 72a, 72b can be eliminated, for example where the tool includes a leading surface that is positioned perpendicular to the central axis A. To this end, FIGS. 13 and 14 illustrate cutting tools 22A and 22B, respectively. Cutting tool 22A of FIG. 13 includes a first interface structure 100a, an opposed, a second interface structure 100b and a proximal end surface 102. The interface structures 100a, 100b can be akin to the interface structures 70a, 70b (FIGS. 4 and 5) discussed above. For example, a first driven surface 106a and a second driven surface 104a are identified for the first interface structure 100a in FIG. 13.

The end surface 102 is bound by first and second side edges 112a and 112b, first and second connecting edges 112c and 112d that form a part of the first interface structure 100a, and third and fourth connecting edges 112e and 112f that form a part of the second interface structure 100b. In the illustrated embodiment, the end surface 102 is substantially planar (i.e., within 5% of a truly planar or flat surface) and extends perpendicular to the central axis; in other embodiments, the end surface 102 can assume other shapes that can be uniform, regular or irregular. The first connecting edge 112c extends from the first side edge 112a toward the central axis A and, in the embodiment illustrated, perpendicular to the second connecting edge 112d. The second connecting edge 112d extends from the first connecting edge 112c to the second side edge 112b. In like manner, the third connecting edge 112e extends from the second side edge 112b toward the central axis A and, in the embodiment illustrated, perpendicular to the fourth connecting edge 112f. The fourth connecting edge 112f extends from the third connecting edge 112e to the first side edge 112a.

The side edges 112a, 112b are positioned at a maximum outer dimension (e.g., diameter) $D_A$ of tool 22' (similar to diameter D in FIG. 6), as calculated as a length of a line extending through the central axis A from the first side edge 112a to second side 112b. First-fourth connecting edges 112c-112f extend perpendicular to the central axis A. In alternative embodiments, one or more of the first-fourth connecting edges 112c-112f are not perpendicular to the central axis A. The second and fourth connecting edges 112d, 112f are illustrated as being parallel to one another and separated by a minimum distance 114 that is approximately half the maximum outer diameter $D_A$ in some embodiments. In one embodiment, the minimum distance 114 is approximately 20-80% of the maximum outer diameter $D_A$ and in other embodiments is approximately 40-60% of the maximum outer diameter $D_A$. The first and third connecting edges 112c, 112e are also illustrated as being parallel to one another, but can be non-parallel to one another in alternative embodiments.

The end surface 102 is reflected as being planar, although in other embodiments the end surface 102 can be arcuate or define other shapes as desired such that end surface 102 may not be truly planar in nature. In some embodiments, surface features can optionally be incorporated into the end surface 102 such that an entirety of the end surface 102 need not necessarily have a constant or uniform shape. However, the end surface 102 generally extends in a direction that is perpendicular to the central axis A. In particular, the end surface 102 can be viewed as defining a major plane extending perpendicular to the central axis A.

The cutting tool 22A also includes an optional axial retention feature in the form of a groove 116. The groove 116 is positioned spaced apart from the end surface 102 and interrupts the interface structures 100a and 100b. Alternatively, the groove 116 (or other retention feature) can be located elsewhere along the tool 22A. The axial retention feature can alternatively be one or more notches, flats, holes, troughs, a biased mechanism, etc. In yet other embodiments, the axial retention feature can be omitted.

The cutting tool 22B of FIG. 14 includes a first interface structure 120a, an opposed, second interface structure (hidden in the view of FIG. 14) and a proximal end projection 122. The interface structures 120a can be akin to the interface structures 70a, 70b (FIGS. 4 and 5) discussed above. For example, a first driven surface 126a and a second driven surface 124a are identified for the first interface structure 120a in FIG. 14. The proximal end projection 122 is defined by a proximal end surface 128, a first recessed surface 130 and a second recessed surface 132 (referenced generally in FIG. 14) opposite the first recessed surface 130.

The end surface 128 is bound by first and second side edges 134a, 134b, as well as first and second connecting edges 134c, 134d. In the illustrated embodiment, the end surface 128 extends perpendicular to a central axis A of the tool 22B. The first connecting edge 134c extends from the first side edge 134a and connects with the second side edge 134b. In like manner, the second connecting edge 134d extends from the first side edge 134a to the second side edge 134b.

The side edges 134a, 134b are positioned at a maximum outer dimension (e.g., diameter) $D_B$ of the tool 22B (similar to diameter D in FIG. 6), as calculated as a length of a line extending through axis A from the first side edge 134a to the second side edge 134b. The connecting edges 134c, 134d extend perpendicular to the central axis A and parallel to one another in some embodiments. In alternative embodiments, the connecting edges 134c, 134d are non-parallel. The connecting edges 134c, 134d are separated by a minimum distance 136 that is approximately half the maximum outer diameter $D_B$ in some embodiments. In one embodiment, the minimum distance 136 is approximately 20-80% of the maximum outer diameter $D_B$ and in other embodiments is approximately 40-60% of the maximum outer diameter $D_B$.

The first recessed surface 130 extends from the first connecting edge 134c to the first interface structure 120a, connecting with (or open to) the first driven surface 126a and with a front end surface 138a of the first interface structure 120a. The second recessed surface 132 is similarly structured to the first recessed surface 130 and relative to the second interface structure (hidden). Each of the surfaces 128, 130 and 132 are illustrated as extending perpendicular to one another and to the central axis A. In other embodiments, the surfaces 128, 130 and 132 do not extend perpendicular to one another.

The surfaces 128, 130 and 132 is reflected as being planar, although in other embodiments the surfaces 128, 130 and 132 can be arcuate or define other shapes as desired such that the surfaces 128, 130 and 132 may not be truly planar in nature. In some embodiments, surface features can optionally be incorporated into the surfaces 128, 130 and 132 such that an entirety of the surfaces need not necessarily have a constant or uniform shape. However, the end surfaces can generally extend in a direction that is perpendicular to the central axis A, whereas the recessed surfaces 130, 132 can generally extend in a direction that is parallel with the central axis A. In particular, the end surface 128 can be viewed as defining a major plane that perpendicular to the central axis A, whereas the recessed surfaces 130, 132 each define a major plane that is parallel with the central axis A.

The cutting tool 22B also includes an axial retention feature in the form of a groove 140. The groove 140 is positioned spaced apart from the end surface 128, adjacent an intersection of the proximal end projection 122 with the interface structures 120a. Alternatively, the groove 140 (or other retention feature) can be located elsewhere along the tool 22B, for example interrupting interface structures 120a. The axial retention feature can alternatively be one or more notches, flats, holes, troughs, a biased mechanism, etc. In yet other embodiments, the axial retention feature can be omitted.

Figure 15:
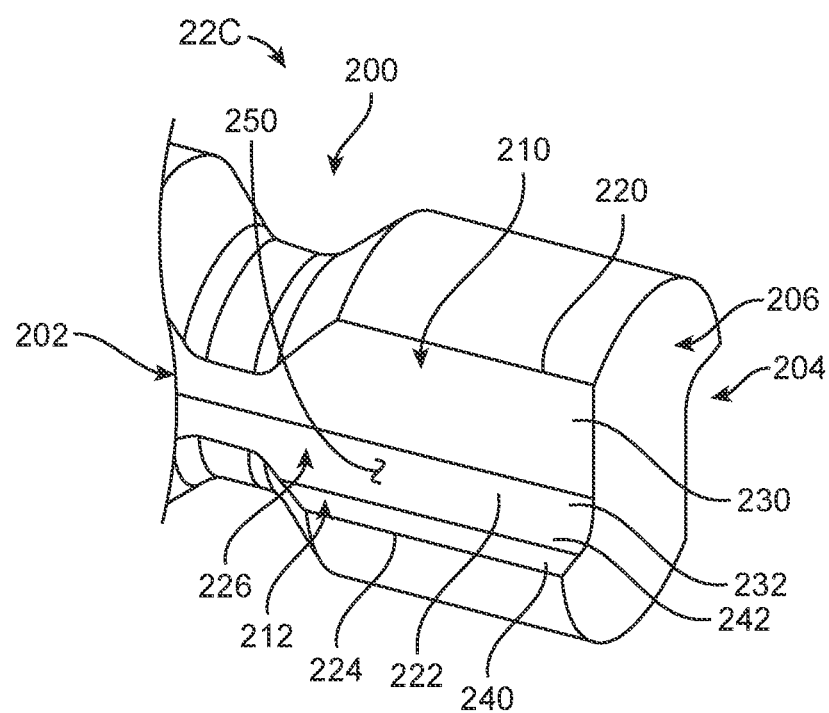
FIG. 15 is an isometric view of a portion of another surgical cutting tool in accordance with principles of the present disclosure.

The surfaces and/or edges associated with the coupling portions of the cutting tools of the present disclosure (e.g., such as the cutting tools 22, 22A, 22B described above) are not limited to linear or uniform shapes. For example, FIG. 15 illustrates portions of another cutting tool 22C in accordance with principles of the present disclosure, in particular a section of a coupling portion 200. The coupling portion 200 includes a first interface structure 202 (referenced generally) and a second interface structure 204 (primarily hidden in the view, and referenced generally). The interface structures 202, 204 can be identical in some embodiments, and can be formed or cut into an optional right cylinder initial shape of the tool 22C. As with previous embodiments, the interface structures 202, 204 are "open" to a proximal end 206 of the tool 22C. With this in mind, FIG. 15 identifies a first driven surface 210 and a second driven surface 212 for the first interface structure 202. The first driven surface 210 is effectively bounded by a first outer longitudinal edge 220 and a connecting longitudinal edge 222. The second driven surface 212 is effectively bounded by a second outer longitudinal edge 224 and the connecting longitudinal edge 222. In addition, a longitudinal groove 226 is defined or formed along the first interface structure 202 that renders the first and second driven surfaces 210, 212 to be non-planar or non-flat. The longitudinal groove 226 can extend an entire longitudinal length of the coupling portion 200, or can extend less than the entire longitudinal length. In other embodiments, the groove 226 can extend in other directions. In yet other embodiments, two or more grooves can be formed.

With the above explanations in mind, the first driven surface 210 can be viewed has having a first region 230 and a second region 232, with the second region 232 effectively being defined by a portion of the longitudinal groove 226. The first region 230 can be substantially planar (i.e., within 5% of a truly planar or flat surface), whereas the second region 232 is not substantially planar. Thus, the first driven surface 210, as a whole, is not substantially planar (e.g., at least along the second region 232). The second driven surface 212 has a similar construction or shape, with a first region 240 being substantially planar, and a second region 242 (defined by a portion of the longitudinal groove 226) that is not substantially planar. Thus, the second driven surface 212, as a whole, is not substantially planar.

The coupling portion 200 can alternatively be viewed as the first driven surface 210 consisting solely of the first region 230, and the second driven surface 212 consisting solely of the first region 240. A surface 250 of the longitudinal groove 226 extends between and interconnects the so-defined driven surfaces 230, 240. The surface 250 of the longitudinal groove 226 thus serves as a connecting edge at an intersection of the driven surfaces 230, 240.

The explanations associated with the surfaces and edges of FIG. 15 are equally applicable to all embodiments of the present disclosure.

In some embodiments, the proximal end 206 can be a substantially flat or planar surface (e.g., perpendicular to a central axis of the tool 22C). In other embodiments, one or more deflection surfaces can be incorporated into the proximal end 206 as described above (e.g., the proximal end 206 can include or define a surface (planar, curved, irregular, etc.) having a major plane that is oblique to the central axis of the tool 22C).

Figure 16A:
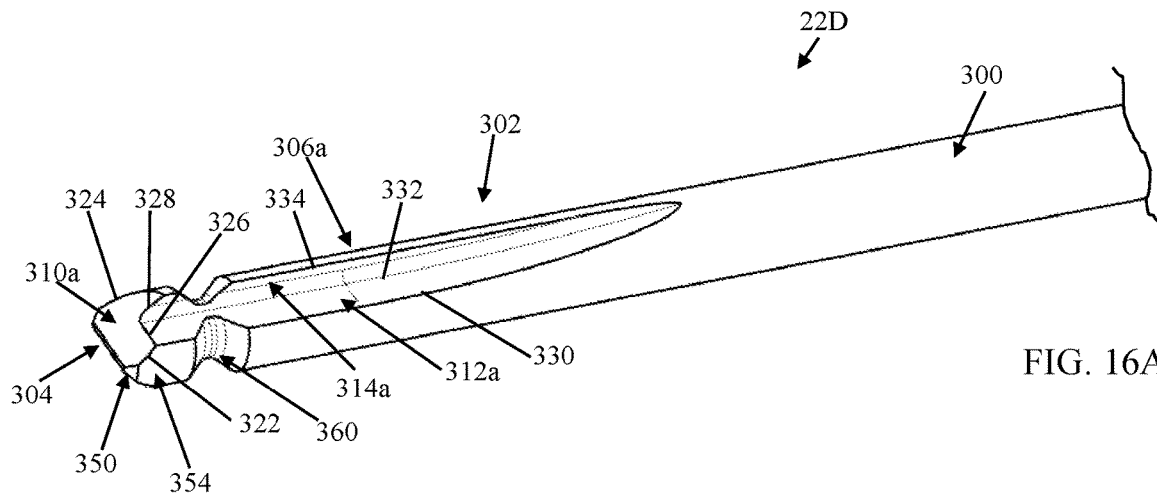
FIG. 16A is an isometric view of a portion of another surgical cutting tool in accordance with principles of the present disclosure.
Figure 16B:
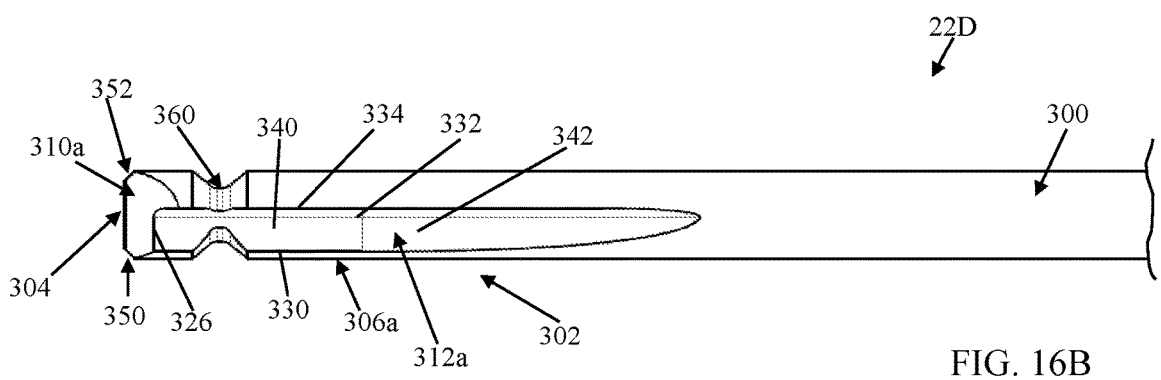
FIG. 16B is a top plan view of the surgical cutting tool of FIG. 16A.
Figure 16C:
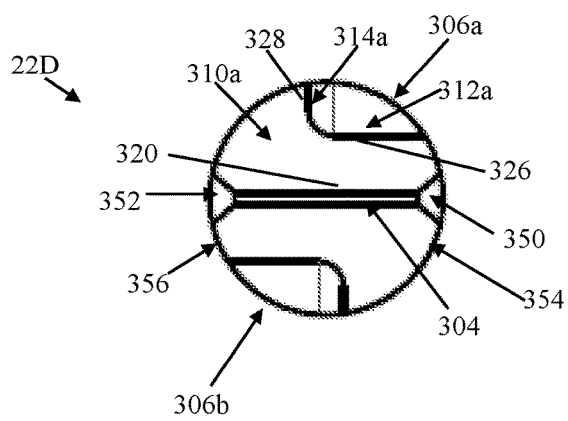
FIG. 16C is an end view of the surgical cutting tool of FIG. 16A.

Portions of another cutting tool 22D in accordance with principles of the present disclosure are shown in FIG. 16A-16C. The cutting tool 22D is highly similar to the cutting tool 22 (FIGS. 4-10) described above, and includes or defines an intermediate stem portion 300 and a proximal coupling portion 302 extending from the stem portion 300 to a proximal end 304. The coupling portion 302 includes a first interface structure 306a (referenced generally) and a second interface structure 306b (hidden in FIGS. 16A and 16B, and referenced generally in FIG. 16C). The interface structures 306a, 306b can be identical (or embodying a mirror image thereof) in some embodiments (symmetrically off-set as with previous embodiments), and can be formed or cut into an optional right cylinder initial shape of the tool 22D.

As identified in the views, the first interface structure 306a includes or defines a deflection surface 310a, a first driven surface 312a, and a second driven surface 314a. The second interface structure 306b can have an identical construction. The deflection surface 310a is bound by a leading edge 320, first and second side edges 322, 324, and first and second intermediate or interposing connecting lateral edges 326, 328. A face of the deflection surface 310a can be substantially planar (i.e., within 5% of a truly planar or flat surface) in some embodiments. In other embodiments, the deflection surface 310a can be arcuate or define other shapes (uniform, regular, irregular, etc.) as desired such that the deflection surface 310a may not be truly planar in nature. In yet other embodiments, surface features can optionally be incorporated into the deflection surface 310a such that an entirety of the deflection surface 310a need not necessarily have a constant or uniform shape. However, a major plane defined by the deflection surface 310a is oriented oblique to a central axis A of the tool 22D (i.e., a major plane of the deflection surface 310a extends at the angle $\beta$ (FIG. 7) with respect to the central axis A as described above).

As with previous embodiments, the driven surfaces 312a, 314a are effectively "open" to the proximal end 304, extending from the connecting lateral edges 326, 328, respectively. For example, the first driven surface 312a is effectively bounded by the first connecting lateral edge 326, a first outer longitudinal edge 330 and a connecting longitudinal edge 332. The second driven surface 314a is effectively bounded by the second connecting lateral edge 328, a second outer longitudinal edge 334 and the connecting longitudinal edge 332. The connecting longitudinal edge 332 can be formed by or include a longitudinal groove, akin to the longitudinal groove 226 (FIG. 15) as described above. In other embodiments, the connecting longitudinal edge 332 can be substantially linear (i.e., within 5% of a truly linear corner or edge). The first driven surface 312a can incorporate any of the shapes, geometries or characteristics described above, as can the second driven surface 314a. For example, a geometry of each of the driven surfaces 312a, 314a can each include a first region 340 (identified for the first driven surface 312a in FIG. 16B) along which at least a portion of the driven surface 312a, 314a is substantially planar (i.e., within 5% of a truly planar or flat surface), and a second or outrun region 342 (identified for the first driven surface 312a in FIG. 16B) along which the driven surface 312a, 314a is curved.

The coupling portion 302 can also include or define opposing chamfer surfaces 350, 352 proximate the proximal end 304. The chamfer surfaces 350, 352 extend from a corresponding guide surface 354, 356 otherwise extending circumferentially between the interface structures 306a, 306b, and reflect a taper in outer diameter of the cutting tool 22D in the proximal direction. That is to say, the guide surfaces 354, 356 combine to define a maximum outer diameter (or other dimension) of the cutting tool 22D at least along the coupling portion 302; the chamfer surfaces 350, 352 represent deviations from the outer diameter of the guide surfaces 354, 356, tapering to the proximal end 304. The chamfer surfaces 350, 352 are distinct from the deflection surfaces 310a, 310b, each defining a major plane that is oblique to a major plane of the deflection surface 310a, 310b of the first and second interface structures 306a, 306b. The chamfer surfaces 350, 352 can further be described as extending between the deflection surface 310a of the first interface structure 306a and the deflection surface 310b of the second interface structure 306b, with the chamfer surfaces 350, 352 being located at opposite sides of the proximal end 304.

The cutting tool 22D also includes an optional axial retention feature in the form of a circumferential groove 360. The circumferential groove 360 is located distally away from the deflection surfaces 310a, 310b such that it interrupts the driven surfaces 312a, 314a of the first interface structure 306a (and of the second interface structure 306b). Alternatively, the circumferential groove 360 (or other retention feature) can be located elsewhere along a length of the cutting tool 22D. The axial retention feature can alternatively be one or more notches, flats, holes, troughs, a biased mechanism, etc. In yet other embodiments, the axial retention feature is omitted.

Figure 17:
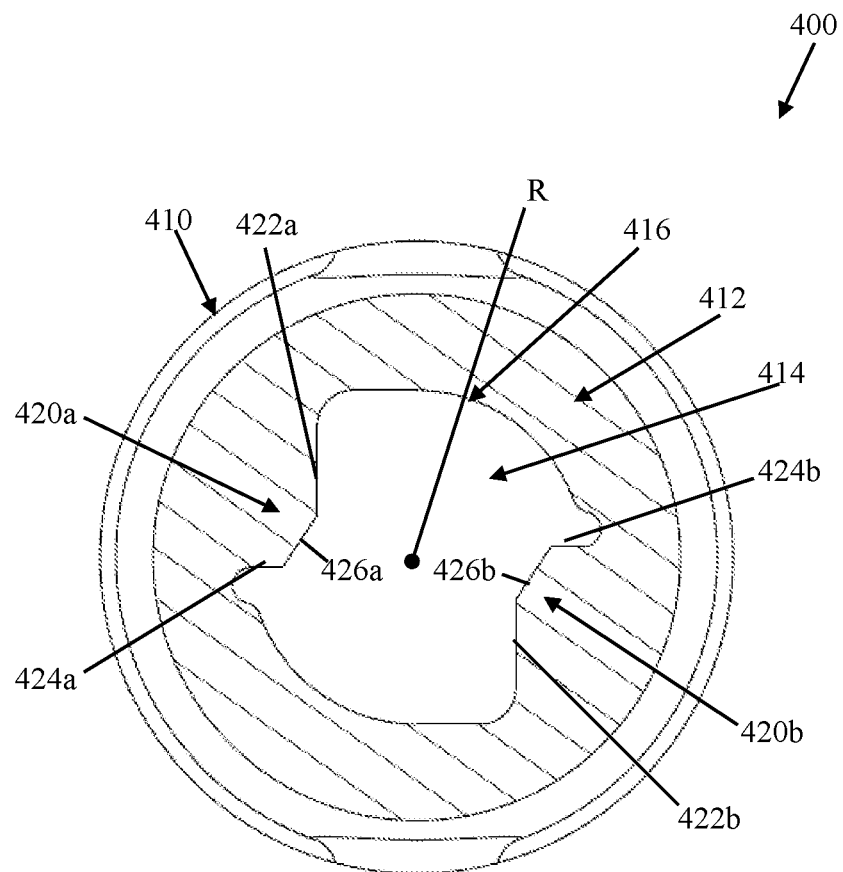
FIG. 17 is a cross-sectional view of a portion of a powered handpiece useful with the present disclosure, including a drive chuck in accordance with principles of the present disclosure.

FIG. 17 illustrates portions of a powered handpiece 400 in accordance with principles of the present disclosure, and useful with any of the cutting tools of the present disclosure (e.g., the cutting tool 22D (FIG. 16A)). The powered handpiece 400 can be highly akin to the powered handpiece 24 (FIG. 1) described above, and any of the previously-described features of the powered handpiece 24 are equally attributable to the powered handpiece 400 except as noted below.

The powered handpiece 400 generally includes a housing 410 and a drive chuck 412. The drive chuck 412 can be connected to or integrally formed with a drive shaft (not shown) of the powered handpiece 400. The drive chuck 412 can have an elongated tubular or hub-like construction, and defines an interior passage 414 sized to receive a cutting tool (e.g., the cutting tool 22D (FIG. 16A)). A maximum diameter of the interior passage 414 (or inner diameter of the drive chuck 412) is defined by a guide face 416, and is selected to be slightly greater than a maximum outer diameter of the cutting tool (e.g., the cutting tool 22D (FIG. 16A)) to be utilized with the powered handpiece 400.

An interior geometry of the drive chuck 412 defines opposed drive pins or drive bodies 420a, 420b that otherwise represent radially inward projections from the guide face 416. Other than being integrated into, or integrally formed with a remainder of, the drive chuck 412, the drive pins 420a, 420b can be highly akin to the drive pins 44a, 44b (FIGS. 2 and 3) described above, and can be identical to each other (or embodying a mirror image thereof). As identified in FIG. 17, then, the first drive pin 420a defines a first drive surface 422a and a second drive surface 424a. The drive surfaces 422a, 424a can each be substantially flat or planar (i.e., within 5% of a flat or planar surface), and are arranged such that a major plane of the first drive surface 422a is substantially perpendicular to a major plane of the second drive surface 424a (i.e., within 5% of a truly perpendicular relationship). In some embodiments, the drive surfaces 422a, 424a do not directly intersect at a singular corner; instead, a recessed surface 426a extends between the drive surfaces 422a, 424a. The second drive pin 420b similarly defines a first drive surface 422b, a second drive surface 424b, and a recessed surface 426b. Though not shown in the view of FIG. 17, the drive pins 420a, 420b can optionally further define a curved leading end commensurate with the descriptions above (e.g., akin the leading end 48a, 48b of FIGS. 2 and 3).

The drive pins 420a, 420b have a symmetrical yet offset arrangement. For example, a major plane defined by the first drive surface 422a of the first drive pin 420a is parallel to, but offset from, a major plane defined by the first drive surface 422b of the second drive pin 420b relative to a rotational axis R of the drive chuck 412. Similarly, a major plane defined by the second drive surface 424a of the first drive pin 420a is parallel to, but offset from, a major plane defined by the second drive surface 424b of the second drive pin 420b relative to the rotational axis R. Other dimensions and geometries of the drive pins 420a, 420b (and in particular the first drive surfaces 422a, 422b and the second drive surfaces 424a, 424b) are complementary with corresponding dimensions and geometries of the cutting tool utilized with the powered handpiece 400.

Figure 18A:
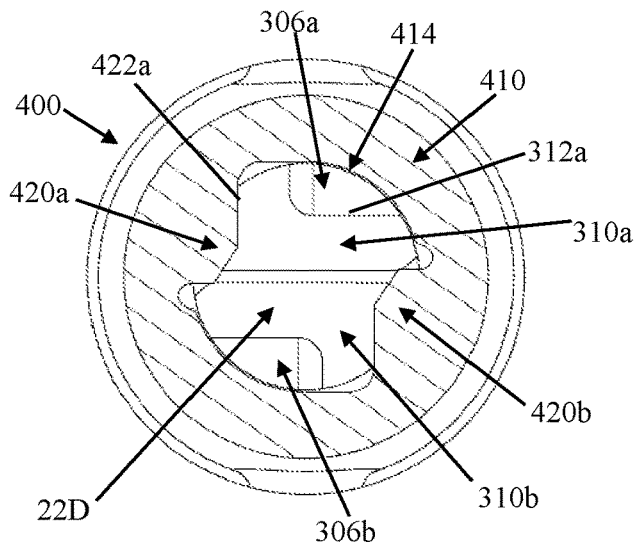
FIGS. 18A-18C illustrate insertion and seating of the surgical cutting tool of FIG. 16A with the drive chuck of FIG. 17.
Figure 18B:
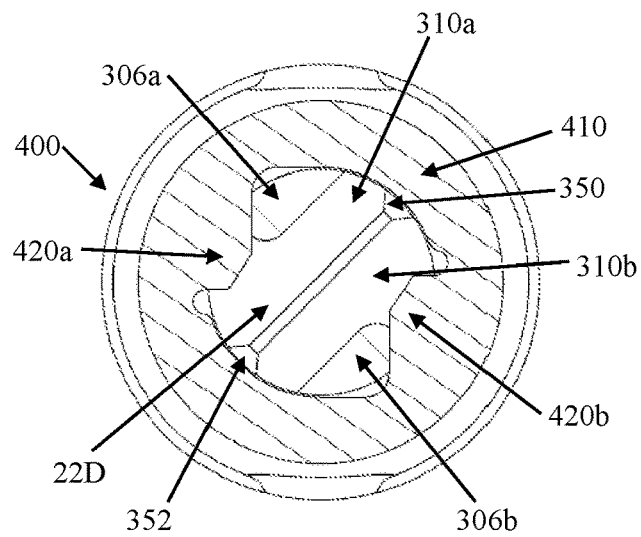
Figure 18C:
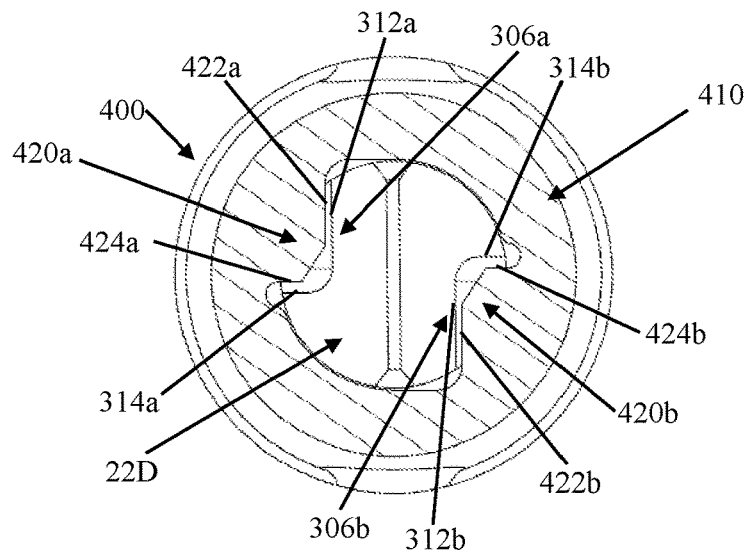

For example, FIGS. 18A-18C illustrate sequential insertion or loading of the cutting tool 22D into the drive chuck 410 viewed from a location proximal the point of insertion of the cutting tool 22D into the powered handpiece 400. In the state of FIG. 18A, the cutting tool 22D has been initially inserted into the interior passage 414 and is being directed toward the drive pins 420a, 420b. As shown, the random rotational arrangement of the cutting tool 22D relative to the drive chuck 410 has randomly located the first and second interface structures 306a, 306b to be rotationally offset from the drive pins 420a, 420b (e.g., the first driven surface 312a of the first interface structure 306a is approximately perpendicular to the first drive surface 422a of the first drive pin 420a). As such, the cutting tool 22D needs to be rotated (e.g., approximately 90 degrees) in order to align the first interface structure 306a with the first drive pin 420a, and the second interface structure 306b with the second drive pin 420b.

With continued application by a user of an insertion force on to the cutting tool 22D (i.e., out of a plane of the page of the views of FIGS. 18A-18C), the deflection surfaces 310a, 310b contacting the leading end (not visible in the views) of the drive pins 420a, 420b. The optional chamfer surfaces 350, 352 can assist in directing the deflection surfaces 310a, 310b into contact with drive pins 420a, 420b. Regardless, with further insertion and as reflected by the intermediate state of FIG. 18B, the insertion force causes contact between the deflection surfaces 310a, 310b and the leading end of the drive pins 420a, 420b, respectively. Due to the angle of the deflection surfaces 310a, 310b relative to a geometry of the leading ends, the cutting tool 22D begins to rotate such that the interface structures 306a, 306b approach rotational alignment with the drive pins 420a, 420b (e.g., due to the cam-like sliding interface described above). This self-aligning interface continues with further insertion of the cutting tool 22D, further rotating the cutting tool 22D relative drive chuck 410 until the first interface structure 306a is aligned with the first drive pin 420a and the second interface structure 306b is aligned with the second drive pin 420b as in FIG. 18C. Once aligned, continued application of the insertion force results in the drive pins 420a, 420b traveling along the corresponding, aligned interface structure 306a, 306b. For example, rotational alignment of the interface structures 306a, 306b with respect to the drive pins 420a, 420b can include the first driven surface 312a of the first interface structure 306a aligned with or slidingly contacting the first drive surface 422a of the first drive pin 420a, as well as alignment between the second driven surface 314a of the first interface structure 306a with the second drive surface 424a of the first drive pin 420a. In a similar manner, the first and second driven surfaces 312b, 314b of the second interface structure 306b are aligned with to the first and second drive surfaces 422b, 424b of the second drive pin 420b. Thus, an axial insertion force continuously applied to the cutting tool 22D causes rotation and subsequent seating of the cutting tool 22D relative to the drive chuck 410. These constructions and methods of the present disclosure are highly convenient for users in that only a single, longitudinal or axial user-applied force is required to couple the cutting tool 22D with the drive chuck 410.

Figure 19:
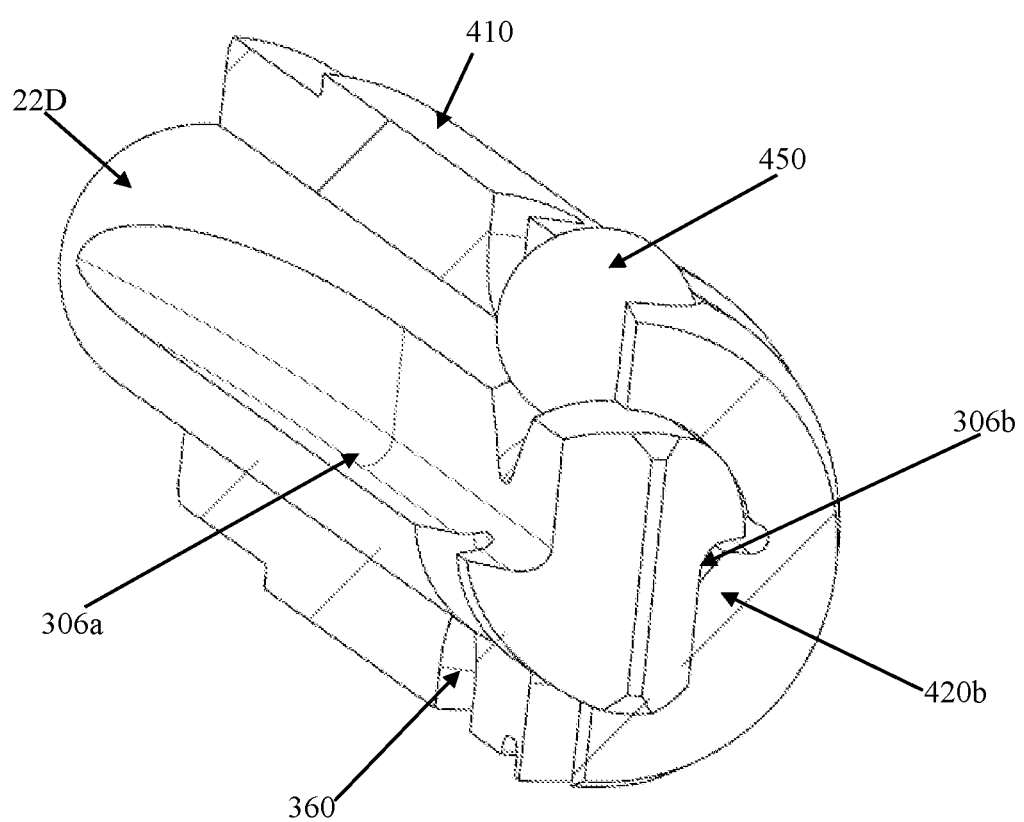
FIG. 19 is an isometric cross-sectional view of the surgical cutting tool of FIG. 16A seated within the drive chuck of FIG. 17.

FIG. 19 further reflects a final, coupled or seated arrangement of the cutting tool 22D and the drive chuck 410. As shown, one or more balls 450 (or other axial retention member) can be maintained by the drive chuck 410 and arranged to engage the circumferential groove 360 of the cutting tool 22D, effectuating an axial lock of the cutting tool 22D relative to the drive chuck 410. Other axial locking interface constructions are equally acceptable that may or may not include the ball 450, and in other embodiments can be omitted. Regardless, a driven interface is established between the drive chuck 410 and the cutting tool 22D. An input torque at the drive chuck 410 is transferred to the cutting tool 22D at the interface structures 306a, 306b. Rotation of the drive chuck 410 in a first direction (clockwise relative to the orientation of FIGS. 18C and 19) transfers a rotational force or torque on to the cutting tool 22D at the interface between the first drive surface 422a of the first drive pin 420a and the first driven surface 312a of the first interface structure 306a, as well as at the interface between the first drive surface 422b of the second drive pin 420b and the first driven surface 312b of the second interface structure 306b. Rotation of the drive chuck 410 in an opposite, second direction (counterclockwise) transfers a rotational force or torque on to the cutting tool 22D at the interface between the second drive surface 424a of the first drive pin 420a and the second driven surface 314a of the first interface structure 306a, as well as at the interface between the second drive surface 424b of the second drive pin 420b and the second driven surface 314b of the second interface structure 306b.

With additional reference to FIG. 2, the drive chucks 40, 410 described above are but some acceptable embodiments envisioned by the present disclosure. The powered handpieces of the present disclosure can incorporate a wide variety of differing drive chuck constructions appropriate for interfacing with the coupling portion associated with the particular surgical cutting tool (e.g., one of skill will recognize that a size and shape of any tool-receiving passage provided with the drive chuck will generally coincide with geometries of the surgical cutting tool, such as any of the surgical cutting tools described above). Further, the powered handpieces of the present disclosure optionally include additional components for rotatably supporting the drive chuck and/or facilitating manual release of the surgical cutting tool. In addition, the drive chucks of the present disclosure in combination with the various embodiment cutting tools can provide tactile feedback to a user during the process of loading the cutting tool to the drive chuck and indicating that the cutting tool has been properly seated; for example, a tactile "click" can be sensed by the user handling the cutting tool as the cutting tool properly seats within the drive chuck.

Rotary surgical cutting tools, powered handpieces, and resultant surgical cutting systems of the present disclosure provide marked improvements over previous designs. The surgical cutting tools with a coupling portion and corresponding powered handpiece drive chuck designs provide superior strength by placing secondary drive surfaces into direct contact with one another. Further, the surgical cutting tools of the present disclosure provide a self-alignment feature with the drive pins of the drive chuck.

Although the present disclosure has been described with reference to preferred embodiments, workers skilled in the art will recognize that changes can be made in form and detail without departing from the spirit and scope of the present disclosure.

What is claimed is:

1. A drive chuck for receiving and supporting any one of a plurality of tools, each tool including a shaft forming a tang providing a coupling portion, the drive chuck comprising:
  a hub-like body defining an interior passage for receipt of a tool tang, the hub-like body carrying one or more balls configured to operably engage a circumferential groove defined within the shaft of the tool and configured to axially lock the tool within the drive chuck upon rotation of the one or more balls within the circumferential groove;
  a guide face defining a maximum diameter of the interior passage;
  a first drive body formed as a radially inward projection from the guide face;
  wherein the first drive body defines a first drive surface and a second drive surface, a major plane of the first drive surface being substantially perpendicular to a major plane of the second drive surface, and wherein, upon insertion of a tool into the drive chuck, a deflection surface defined on the shaft of the tool contacts the first drive body such that an insertion force causes the tool to rotate about a central axis of the tool and aligns a first driven surface of the tool with the first drive surface and the second driven surface of the tool with the second drive surface, once the driven surfaces are aligned, the balls of the hub-like body engage within the circumferential grooves to axially lock the tool within the drive chuck upon rotation of the hub-like body.

2. The drive chuck of claim 1, wherein the interior passage and the first drive body are of a prescribed size and configuration for receipt and support of the tang of any one of the plurality of tools.

3. The drive chuck of claim 1, wherein the first drive body further includes a recessed surface extending between the first and second drive surfaces.

4. The drive chuck of claim 1, wherein the first drive surface is substantially flat.

5. The drive chuck of claim 4, wherein the second drive surface is substantially flat.

6. The drive chuck of claim 1, further comprising a second drive body apart from the first drive body and formed as a radially inward projection from the guide face.

7. The drive chuck of claim 6, wherein the second drive body defines a first drive surface and a second drive surface, a major plane of the first drive surface of the second drive body being substantially perpendicular to a major plane of the second drive surface of the second drive body.

8. The drive chuck of claim 7, wherein relative to a rotational axis of the drive chuck, the major plane of the first drive surface of the first drive body is parallel to, but offset from, the major plane of the first drive surface of the second drive body.

9. The drive chuck of claim 8, wherein relative to the rotational axis, the major plane of the second drive surface of the first drive body is parallel to, but offset from, the major plane of the second drive surface of the second drive body.

10. The drive chuck of claim 9, wherein none of the major planes intersect the rotational axis.

11. The drive chuck of claim 1, wherein the drive chuck defines an insertion side at which the tang of the tool is inserted, and further wherein a leading end of the first drive body faces the insertion side, and even further wherein the leading end is curved.

12. A surgical system for cutting tissue, the system comprising:
  a powered handpiece including:
    a housing,
    a drive chuck disposed within the housing, the drive chuck including:
      a hub-like body defining an interior passage for receipt of a tool tang, the hub-like body carrying one or more balls configured to operably engage a circumferential groove defined within a shaft of the tool and configured to axially lock the tool within the drive chuck upon rotation of the one or more balls within the circumferential groove;
      a guide face defining a maximum diameter of the interior passage;
      a first drive body formed as a radially inward projection from the guide face;
      wherein the first drive body defines a leading end, a first drive surface and a second drive surface, a major plane of the first drive surface being substantially perpendicular to a major plane of the second drive surface; and
  a tool releasably connectable to the powered handpiece, the tool including:
    an elongated shaft defining a central axis, a first end, a second end opposite the first end, and a tang adjacent the second end, the tang providing a coupling portion;
    wherein the coupling portion extends from a first position spaced apart from the second end to a second position at the second end, the coupling portion defining a leading edge, a first deflection surface extending from the leading edge, and a first interface structure including a first driven surface connected to and extending from the first deflection surface, and a second driven surface connected to and extending from the first deflection surface and the first driven surface;
    wherein upon insertion of the tang into the drive chuck, the first deflection surface contacts the leading end of the first drive body such that an insertion force causes the tool to rotate about the central axis and align the first driven surface with the first drive surface and the second driven surface with the second drive surface, once the driven surfaces are aligned, the balls of the hub-like body engage within the circumferential grooves to axially lock the tool within the drive chuck upon rotation of the hub-like body.

13. The surgical system of claim 12, wherein the tool further defines a dissection portion adjacent the first end.

14. The surgical system of claim 12, wherein the drive chuck further comprises a second drive body apart from the first drive body and formed as a radially inward projection from the guide face.

15. The surgical system of claim 14, wherein the second drive body defines a leading end, a first drive surface and a second drive surface, a major plane of the first drive surface of the second drive body being substantially perpendicular to a major plane of the second drive surface of the second drive body.

16. The surgical system of claim 15, wherein relative to a rotational axis of the drive chuck, the major plane of the first drive surface of the first drive body is parallel to, but offset from, the major plane of the first drive surface of the second drive body.

17. The surgical system of claim 16, wherein relative to the rotational axis, the major plane of the second drive surface of the first drive body is parallel to, but offset from, the major plane of the second drive surface of the second drive body.

18. The surgical system of claim 17, wherein the coupling portion further defines a second deflection surface extending from the leading edge, and a second interface structure including a first driven surface connected to and extending from the second deflection surface, and a second driven surface connected to and extending from the second deflection surface and the first driven surface of the second interface structure, and even further wherein upon insertion of the tang into the drive chuck, the second deflection surface contacts the leading end of the second drive body such that an insertion force causes the tool to rotate about the central axis and align the first driven surface of the second interface structure with the first drive surface of the second drive body and the second driven surface of the second interface structure with the second drive surface of the second drive body.

* * * * *